United States Patent
Martin et al.

(10) Patent No.: US 7,786,156 B2
(45) Date of Patent: Aug. 31, 2010

(54) SYNTHESIS METHODS AND INTERMEDIATES FOR THE MANUFACTURE OF RIZATRIPTAN

(75) Inventors: Pierre Martin, Rheinfelden (CH); Ulrich Berens, Binzen (DE); Andreas Boudier, Basel (CH); Oliver Dosenbach, Bad Bellingen (DE)

(73) Assignee: ratiopharm GmbH, Ulm (DE)

( * ) Notice: Subject to any disclaimer, the term of this patent is extended or adjusted under 35 U.S.C. 154(b) by 812 days.

(21) Appl. No.: 10/586,958

(22) PCT Filed: Jan. 27, 2005

(86) PCT No.: PCT/EP2005/000793

§ 371 (c)(1),
(2), (4) Date: Nov. 28, 2006

(87) PCT Pub. No.: WO2005/075422

PCT Pub. Date: Aug. 18, 2005

(65) Prior Publication Data

US 2007/0123711 A1    May 31, 2007

Related U.S. Application Data

(60) Provisional application No. 60/543,463, filed on Feb. 10, 2004.

(30) Foreign Application Priority Data

Jan. 28, 2004    (EP) .................................. 04100303

(51) Int. Cl.
*A61K 31/41* (2006.01)
*C07D 249/00* (2006.01)
*C07D 249/08* (2006.01)
(52) U.S. Cl. .................................. 514/383; 548/262.2
(58) Field of Classification Search ................. 514/383; 548/262.2
See application file for complete search history.

(56) References Cited

U.S. PATENT DOCUMENTS 4,556,717 A    12/1985    Wetter et al.
5,510,359 A    4/1996    Castro Pineiro et al.

FOREIGN PATENT DOCUMENTS

EP        0 497 512 A2      8/1992
WO       WO 95/32197         11/1995
WO       WO 2004/014877 A1 *  2/2004
WO       WO 2004/056769 A2   7/2004

OTHER PUBLICATIONS

Written Opinion of the International Searching Authority issued in PCT/EP05/000793(2005).

* cited by examiner

*Primary Examiner*—Susannah Chung
(74) *Attorney, Agent, or Firm*—Chalin A. Smith; Smith Patent Consulting, LLC

(57) ABSTRACT

The invention relates to a process for the manufacture of an 1,2,4-triazol-1-yl compound of the formula [A],

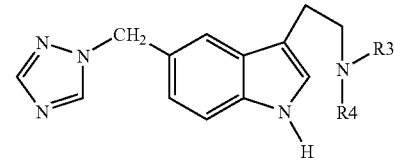

or a salt thereof, wherein each of R3 and R4 is hydrogen or lower alkyl, said process comprising reacting a hydrazine compound of the formula [B]

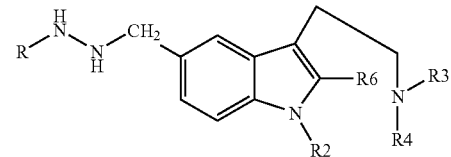

wherein R is hydrogen or acyl, R2 is hydrogen or a protecting group, are hydrogen or lower alkyl, and R6 is hydrogen or COOR7, or a salt thereof, with a 1,2,4-triazolyl forming reagent.

In addition, novel intermediates for the synthesis of the antimigraine agent Rizatriptan and methods for their synthesis are presented.

20 Claims, No Drawings

SYNTHESIS METHODS AND INTERMEDIATES FOR THE MANUFACTURE OF RIZATRIPTAN

This application is a Rule 371 U.S. National Phase Filing of PCT/EP05/000793, filed Jan. 27, 2005, which, in turn, claims priority to European Patent Application No. 04.100303.9, filed Jan. 28, 2004 and U.S. Provisional Patent Application Ser. No. 60/543,463, filed Feb. 10, 2004, the contents of which are incorporated by reference herein in their entirety.

SUMMARY OF THE INVENTION

The present invention provides a novel process for the manufacture of tryptamine derivatives such as Rizatriptan, as well as novel intermediates for said process and novel processes for preparing the intermediates. Rizatriptan and the related derivatives are known to be pharmaceutically useful, e.g. in the treatment of migraine.

BACKGROUND OF THE INVENTION

A number of ways are known for the synthesis of Rizatriptan (=3-[2-(dimethylamino)ethyl]-5-(1,2,4-triazol-1-ylmethyl)indole), and salts thereof, such as the benzoate. Rizatriptan is useful in the treatment of migraine. One known way (see EP 0 497 512 A2) for the synthesis is as follows: Alkylation of 1,2,4-triazol with 4-nitrobenzylchloride 1 leads to a mixture of two products resulting from alkylation of either the 1- or the 4-position of the triazole. The undesired 4-alkylation product can be removed (see *Tetrahedron Lett.* 1994, 35, 6981) or its formation can be avoided by alkylation of 4-amino-1,2,4-triazol and the subsequent removal of the 4-amino group by diazotation (see EP 0 573 221). Catalytic hydrogenation of the nitro group of 2 yields aniline 3 in quantitative amounts. Still it would be desirable to avoid the formation of the undesired 4-alkylation product, which is one of the problems to be solved by the present invention.

Diazotation of 3 and reduction of the diazonium salt with excess tin(II)chloride results in the phenyl hydrazone 6 (see *J. Med. Chem.* 1995, 38, 1799). However, tin salts are of low acceptability especially for pharmaceuticals, and in the form of sodium sulphite a more acceptable reducing agent was identified (see EP 0 573 221 A1).

The reaction of 6 or a salt of it under acidic conditions with aldehyde 5a or an acetal thereof produces, depending on the detailed reaction conditions, the tryptamine derivatives 4a or 4b, while with aldehyde 5b or an acetal thereof. Rizatriptan is directly obtained. Using 5b is preferable, as in this case Rizatriptan is obtained directly, though the synthesis via the dimethyl acetal of 5b requires additional steps (see *J. Org. Chem.* 1994, 59, 3738), whereas alkylation of dimethyl-amine with 4a or the reductive methylation of 4b give Rizatriptan only in relatively low yields.

The conversion of 3 into 6 and the subsequent Fischer-Indolisation with 5b may also be combined into a one-pot procedure (see EP 0 573 221 A1) to produce, after chromatography, Rizatriptan in 45% yield.

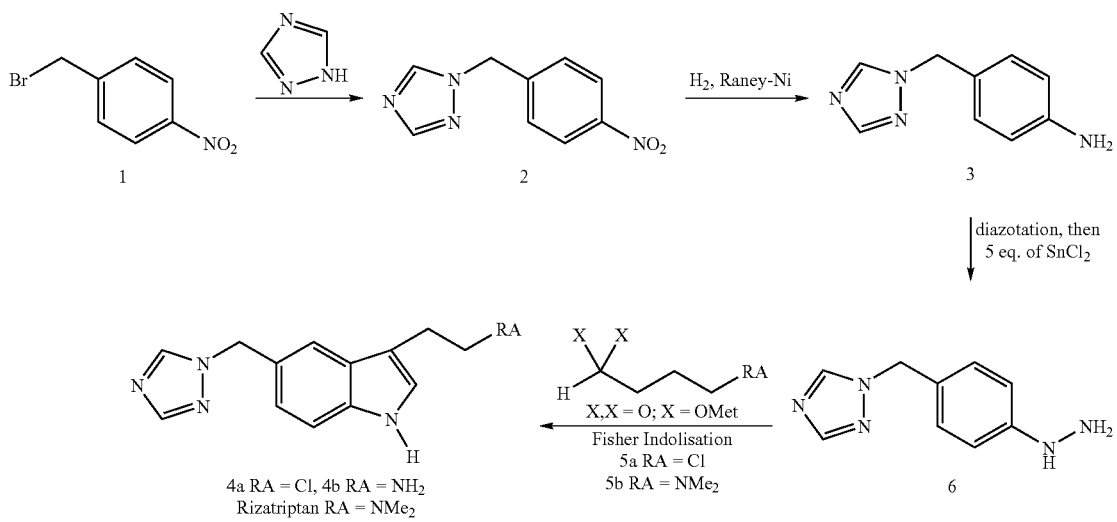

The low yields in the indole forming reaction have been attributed to "triazol polymerization", the avoidance of which is another problem to be solved by the present invention, and led to other approaches (see WO 95/32197). There, a 2-iodo aniline such as 7, which is obtained via iodination of 3, is reacted with an alkyne 8 (with TES representing triethylsilyl) in the presence of a homogenous Pd-catalyst to give a mixture of the protected tryptopholes 9 and 10. These can be separated without a need for chromatography, and after deprotection of 9 the corresponding tryptophol can be transformed into Rizatriptan in 73% yield.

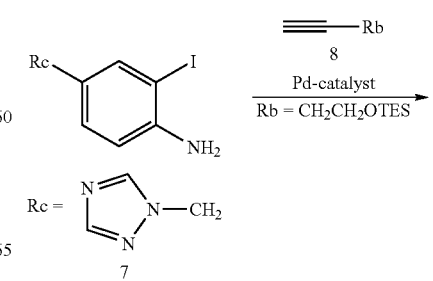

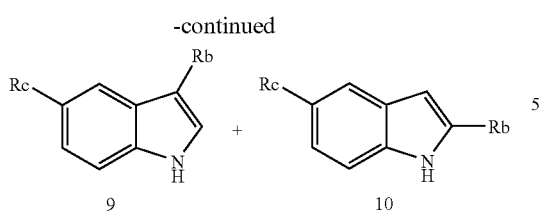

Although no additives such as triphenyl phosphine are required, a rather high loading of expensive homogenous palladium (e.g. 2 to 3 mol-%) is required to convert 7 into 9 and 10. Avoidance of the use of such a high palladium amount is another problem to be solved by the present invention.

Another approach to overcome the problems due to "triazole polymerisation" utilizes the Pd-catalysed coupling of a 2-halo or 2-trifluormethansulfonyl substituted aniline with an acyl silane. After de-silylation of the obtained 2-silyl indole derivatives, tryptanes such as Rizatriptan can be obtained (U.S. Pat. No. 5,808,064) (as well as Zolmitriptan, Almitriptan or Sumatriptan). Though this procedure is efficient, it suffers from the fact that acyl silanes are not readily available and still soluble (homogenous) palladium catalysts in high amount (e.g. 2 to 3 mol-%) are required. One of the problems to be solved by the present invention is to avoid the acyl silanes and the homogenous palladium catalysts.

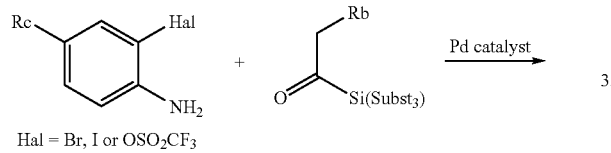

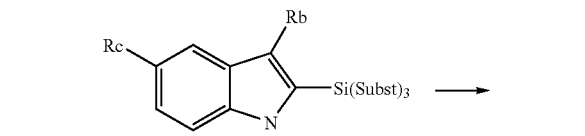

The present invention presents a solution for the preparation of Rizatriptan, which avoids the disadvantages mentioned above associated with the Fischer indolisation procedure and also avoids the use of homogeneous palladium catalysts, thus especially solving the above-mentioned problems and offering further synthesis advantages.

GENERAL DESCRIPTION OF THE INVENTION

A surprisingly simple approach to tryptophanes has been identified by converting a substituted isatine such as 11 into an amide such as 12, and the subsequent (optionally one-pot) reduction of the latter into the tryptamine 13 (see WO 2004/056769 which is incorporated by reference in its entirety, or especially in this regard)

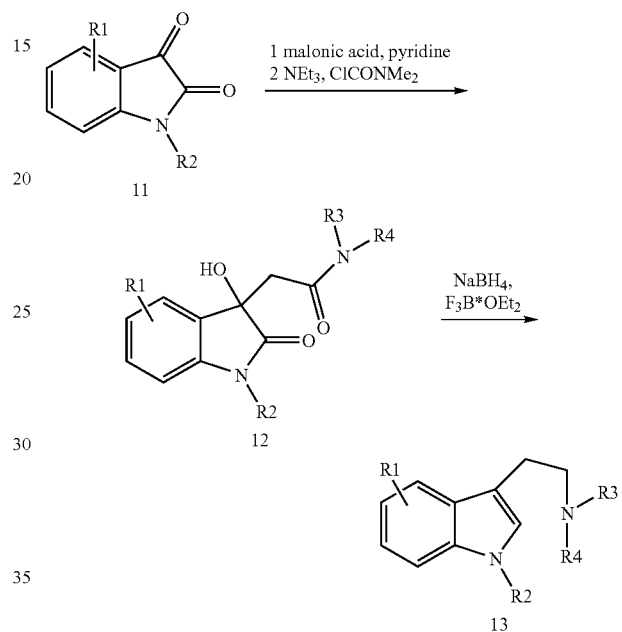

R1 is hydrogen or a substituent such as cyano or a group selected from halogen or an aryl ester of a substituted sulfonic acid, and R2, R3 and R4, where present, respectively, preferably have the meanings defined below.

Of particular interest are compounds where R1 is a cyano group, such as 14, which is readily available by the methods described e.g. in U.S. Pat. No. 5,510,359 or in Ciba Patent Application WO 2004/056769 (which is incorporated by reference especially in this regard).

It has now been found surprisingly that when a nitrile compound such as 14 is reacted under hydrogenation in the presence of hydrazine 15a (R=H) or an R=acyl protected hydrazine such as N-formyl hydrazine 15b or N-acetyl hydrazine 15c the corresponding hydrazones 16a-c or 18a-c respectively are obtained, this reaction offering a new route for the synthesis of tryptamines:

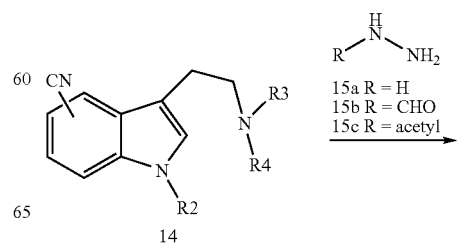

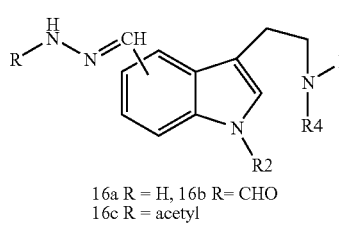

16a R = H, 16b R= CHO
16c R = acetyl

The whole conversion of a nitrile to the hydrazine via the hydrazone follows the general scheme below.

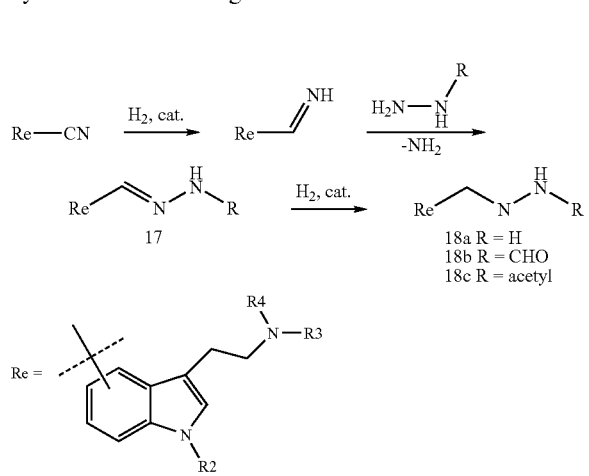

wherein R is hydrogen, formyl or acetyl or most generally acyl.

Alternatively, the hydrazones 17 or the hydrazines 18 can be obtained by reaction of aldehyde 19 (obtainable e.g. according to U.S. Pat. No. 5,510,359 or according to WO 2004/056769 which are herewith incorporated by reference preferably regarding this aspect) with the hydrazines 15a, 15b or 15c, to give 17a-c, followed by reduction to give 18a-c.

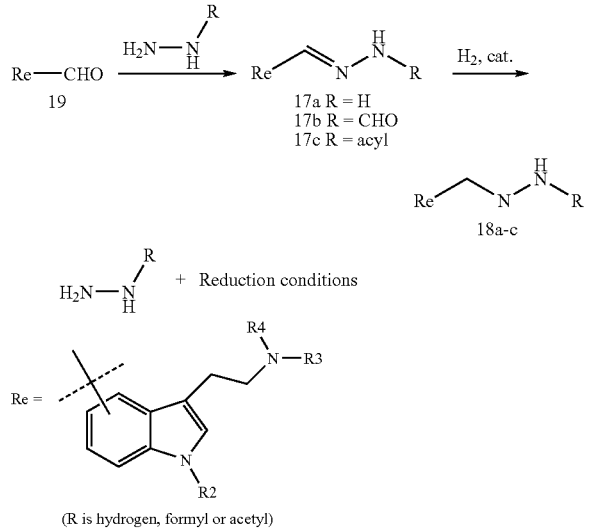

(R is hydrogen, formyl or acetyl)

Further, carbonic acid hydrazides such as 20 can also be converted into a hydrazine such as 20a by means of said borane reduction protocol:

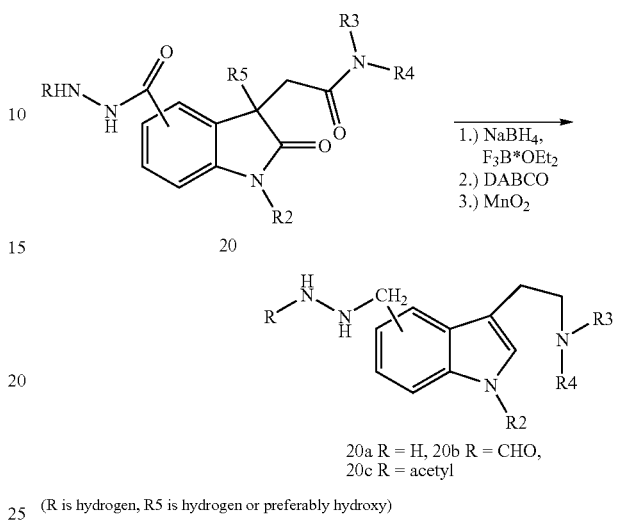

(R is hydrogen, R5 is hydrogen or preferably hydroxy)

These and related ways described in detail below allow for the synthesis of Hydrazines 20a, 20b or 20c.

Hydrazines, such as 20a, 20b or 20c can then, in the most general and most important aspect of the invention, be converted efficiently into 1-substituted 1,2,4-triazoles, especially by reacting them with either a formamidinium salt (acetate or chloride) (see e.g. *Chem. Ber.* 1981, 114, 2825), or with Gold's reagent (see e.g. *J. Med. Chem.* 1992, 35, 2392), or also with 1,3,5-triazine in a suitable solvent (see e.g. *J. Org. Chem.* 1956, 21, 1037), or in analogy to the methods described for different hydrazines in U.S. Pat. No. 4,556,717.

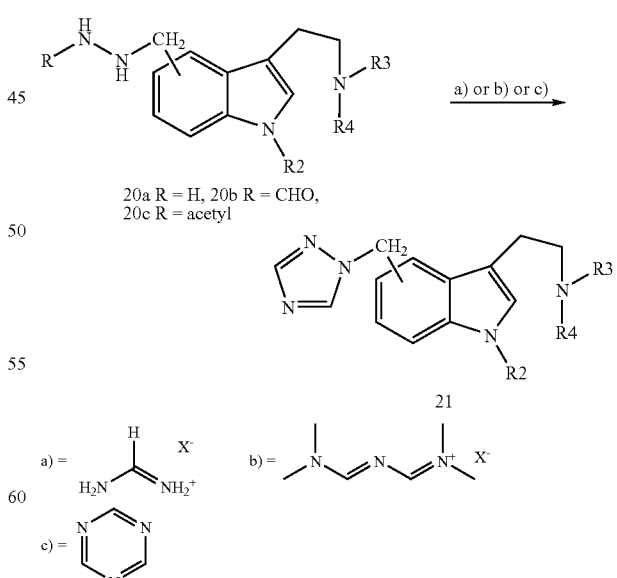

The final product, either obtained in free form or in salt form or after transformation of the free form into a salt or a salt into a different salt, is preferably Rizatriptan 21 (R2=H, R3=R4=CH₃) or a salt thereof.

DETAILED DESCRIPTION OF THE INVENTION

The invention relates in a first embodiment to a process for the manufacture of an 1,2,4-triazol-1-yl compound of the formula [A],

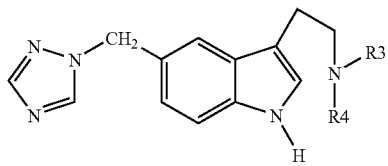

[A]

or a salt thereof,
wherein
each of R3 and R4 is hydrogen or preferably lower alkyl
said process comprising
reacting a hydrazine compound of the formula [B]

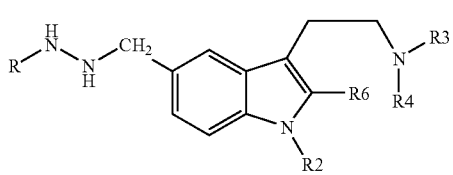

[B]

wherein
R is hydrogen or acyl
R2 is hydrogen or (less preferably) a protecting group, R3 and R4 have the meanings as defined above for compounds of the formula [A], and R6 is hydrogen or is a group COOR7, with R7 being hydrogen or one equivalent of a cation or a suitable hydrocarbon residue, or a salt thereof with a 1,2,4-triazolyl forming reagent, where R is acyl in formula [B], preferably removing an acyl group R before the reaction of the compound of the formula [B] with the 1,2,4-triazolyl forming reagent e.g. by hydrolysis or catalytic hydrogenation,
if present removing any protecting group R2 and removing any group COOR7 to produce the free compound, or a salt, of a compound of the formula [A],
and, if desired, converting a salt of a resulting compound of the formula [A] into a free form of a compound of the formula [A], converting a resulting free form of a compound of the formula [A] into a (preferably pharmaceutically acceptable) salt or converting a salt of a compound of the formula [A] into a different (preferably pharmaceutically acceptable) salt.

Preferably, in the process described in the last paragraph, R in the compound of formula [B] is hydrogen and/or lower alkanoyl, especially acetyl or formyl. Lower alkanoyl apart from formyl advantageously is hydrolytically removed prior to the reaction with the triazol forming agent (e.g. formamidinium salts or derivatives), and preferably in each of formulae [A] and [B] each of R3 and R4 is methyl and the compound of the formula [A] is produced in free form or in the form of a pharmaceutically acceptable salt. Preferably, residue R6 is hydrogen. If residue R is an acyl group which is different from a formyl group it is preferred to remove this group before the reaction of the compound of formula [B] with the 1,2,4-triazolyl forming reagent. Of course, if residue R is a formyl group, this group can also be removed before the reaction of the compound of formula [B] with the 1,2,4-triazolyl forming reagent.

In a further embodiment, the invention relates to a process for the manufacture of a compound of the formula [B] as shown above, or a salt thereof, wherein R, R2, R3, R4 and R6 are as defined above, comprising reacting a compound of the formula [D],

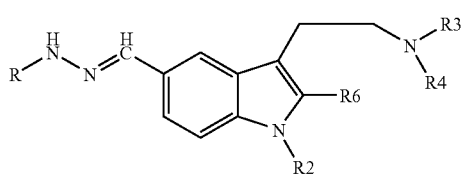

[D]

wherein R, R2, R3 and R4 are as just defined, or a salt thereof, under reductive conditions to a compound of the formula [B], or a salt thereof. The invention, in a further embodiment, also relates to a process for the manufacture of a compound of the formula [D] shown above, wherein R, R2, R3 and R4 are as defined in the first or preferably in the second of the preceding paragraphs and residue R6 is hydrogen, said process comprising reacting a compound of the formula [E],

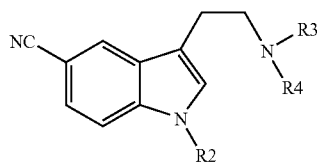

[E]

wherein each of R2, R3 and R4 is as defined above, or a salt thereof with a hydrazine of the formula [F],

R—NH—NH₂                                                  [F]

wherein R is hydrogen or acyl, preferably hydrogen or lower alkanoyl (which is more preferably acetyl or especially formyl), or a salt thereof, under reductive conditions to a compound of the formula [D] as defined above, or a salt thereof.

The invention also relates to a compound of the formula [D] as shown above, wherein R, R2, R3 and R4 are as defined there, more preferably wherein R is hydrogen or acyl, R2 is hydrogen or a protecting group, preferably hydrogen, and each of R3 and R4 is hydrogen or preferably lower alkyl, more preferably methyl, or a salt thereof.

In yet another embodiment, the invention relates to a process for the manufacture of a compound of the formula [E] as shown above, wherein R2 is hydrogen or a protecting group, preferably hydrogen, and each of R3 and R4 is hydrogen or preferably lower alkyl, more preferably methyl, or a salt thereof, comprising reacting a compound of the formula [G], or a salt thereof,

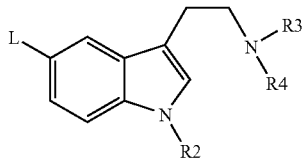

[G]

wherein R2, R3 and R4 are as defined above and L is halogen, unsubstituted or substituted alkanesulfonyloxy or arylsulfonyloxy, with a cyanide salt (e.g. Zn(CN)₂ in the presence of a homogenous palladium catalyst; and alkali metal cyanide in the presence of a Ni(O) complex; or copper(I)cyanide) optionally in the presence of a catalyst, to the compound of the formula [E] as defined above, or a salt thereof.

The manufacture of a compound of the formula [G] as shown above, or a salt thereof, wherein L, R2, R3 and R4 are as defined above, preferably comprises reducing a compound of the formula [H],

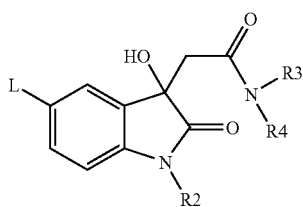

[H]

wherein L, R2, R3 and R4 are as defined above, in the presence of borane, which is preferably obtained in situ from sodium boro hydride and a lewis acid, and subjecting the resulting product(s) to removal of borane from any amino borane intermediates and to a subsequent oxidation/de-hydrogenation with an oxidant, for example a quinone or preferably manganese dioxide, in order to yield a compound of the formula [G], or a salt thereof, as defined above;

where the compound of the formula [H] is preferably manufactured by process a) or process b) as defined below.

a) A compound of the formula [I],

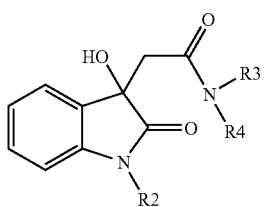

[I]

wherein R2 is a protecting group or preferably hydrogen, and each of R3 and R4 is hydrogen or preferably lower alkyl, more preferably methyl, is reacted with an electrophile capable of introducing group L, especially halogen, preferably is reacted with a halo-succinimide, resulting in a corresponding compound of the formula [H]. The compound of the formula [I] is preferably formed by reacting a compound of the formula [K],

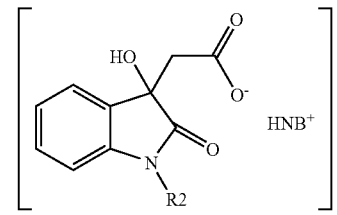

[K]

wherein R2 is a protecting group or preferably hydrogen and NB is a tertiary nitrogen base where the nitrogen is not part of a ring, with a compound of the formula [L],

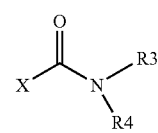

[L]

wherein X is halogen and R3 and R4 are as defined above, to give the compound of the formula [I] as defined above.

The compound of the formula [K] is preferably obtained by reacting an isatine compound of the formula [M],

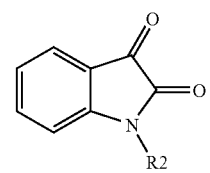

[M]

wherein R2 is a protecting group or preferably hydrogen, with malonic acid in the presence of a pyridine, especially pyridine and/or one or more picolines, in the absence or presence of a N,N-di-(lower alkyl)-lower alkanoylamide, a lower alkanol, e.g. methanol or ethanol, or a di-lower alkylsulfoxide, e.g. dimethylsulfoxide, especially N,N-dimethyl formamide, advantageously in the additional presence of an ester, preferably a lower alkyl alkanoate, more preferably ethyl acetate as a cosolvent, followed by conversion of the resulting compound which is present as a salt of a pyridine into the salt of the base NB given in formula [K], where preferably the reaction of the isatine compound of the formula [M] and the conversion of the product salt of a pyridine into the corresponding salt of the formula [K] and more preferably also the reaction of a compound of the formula [K] with a compound of the formula [L] to a compound of the formula [I] take place in the same reaction vessel;

b) More preferably a compound of the formula [K*],

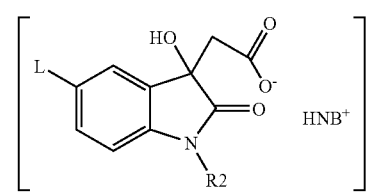

[K*]

wherein R2 is a protecting group or preferably hydrogen, L is a leaving group, preferably selected from halogen, unsubstituted or substituted alkanesulfonyloxy or arylsulfonyloxy, and NB is a tertiary nitrogen base where the nitrogen is not part of a ring is reacted with a compound of the formula [L] as defined, above, to obtain the compound of the formula [H] as defined above.

The compound of the formula [K*] is preferably obtained by reacting an isatine compound of the formula [M*],

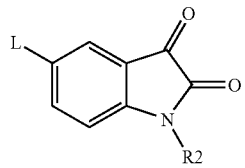

[M*]

wherein R2 is as defined above and L is a leaving group as defined above, with malonic acid in the presence of a pyridine, especially pyridine and/or one or more picolines in the absence or presence of a N,N-di-(lower alkyl)-lower alkanoylamide, a lower alkanol, e.g. methanol or ethanol, or a di-lower alkylsulfoxide, e.g. dimethylsulfoxide, especially N,N-dimethyl formamide, advantageously in the presence of an ester, preferably lower alkyl alkanoate, especially ethyl acetate as a cosolvent, followed by conversion of the resulting compound which is present as a salt of a pyridine into the salt of the base NB given in formula [K*], where the reaction of the isatine compound of the formula [M*] and the conversion of the product salt of a pyridine into the corresponding salt of the formula [K*] preferably take place in the same reaction vessel.

Yet another embodiment of the invention relates to a process for the manufacture of a compound of the formula [B] as shown above, wherein R is hydrogen, R2 is hydrogen or a protecting group, and each of R3 and R4 is hydrogen or lower alkyl, or a salt thereof, comprising reducing a compound of the formula [C],

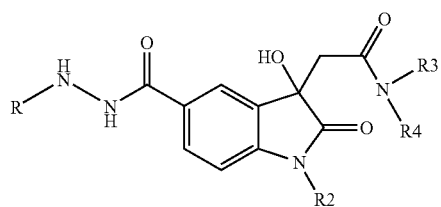

[C]

wherein R is hydrogen, R2 is a protecting group or preferably hydrogen and each of R3 and R4 is hydrogen or preferably lower alkyl, more preferably methyl, or a salt thereof, in the presence of borane, which is preferably obtained in situ from sodium boro hydride and a lewis acid, and subjecting the resulting product(s) to removal of borane from any amino borane intermediates and to a subsequent oxidation/de-hydrogenation with manganese dioxide, thus producing a compound of the formula [B] as just defined, or a salt thereof.

The invention also relates to a compound of the formula [C] as shown above, wherein R is acyl such as lower acyl or preferably hydrogen, R2 is a protecting group or preferably hydrogen, and each of R3 and R4 is hydrogen or preferably lower alkyl, more preferably methyl, or a salt thereof.

A further embodiment of the invention relates to a process for the manufacture of a compound of the formula [C] as shown above, or a salt thereof, wherein R, R2, R3 and R4 are as defined above, comprising reacting a compound of the formula [N],

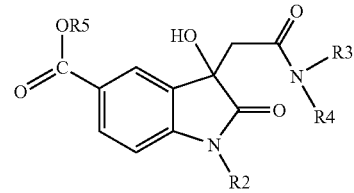

[N]

wherein R2, R3 and R4 are as defined above and R5 is unsubstituted or substituted alkyl, preferably lower alkyl, more preferably methyl or ethyl, with a hydrazine of the formula [F]

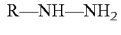

R—NH—NH$_2$     [F]

wherein R is acyl, preferably lower alkanoyl, such as acetyl or formyl, or most preferably hydrogen, or a salt thereof, to a corresponding compound of the formula [C].

A further embodiment of the invention relates to a process for the manufacture of a compound of the formula [N] as shown above, wherein R2 is a protecting group or preferably hydrogen, and each of R3 and R4 is hydrogen or preferably lower alkyl, more preferably methyl, comprising reacting a compound of the formula [H] as shown above, wherein R2, R3 and R4 are as just defined, and L is as defined above, by reaction with carbon monoxide in the presence of the corresponding alcohol R5-OH in the presence of a catalyst and a tertiary nitrogen base, to the compound of the formula [N] as just defined, where the compound of the formula [H] is preferably manufactured as described above.

A further embodiment of the invention relates to a process for the manufacture of a compound of the formula [B] as shown above, or a salt thereof, wherein R is acyl, preferably lower alkanoyl, more preferably formyl or acetyl, or hydrogen, R2 is a protecting group or preferably hydrogen, and each of R3 and R4 is hydrogen or preferably lower alkyl, more preferably methyl comprising reacting an aldehyde of the formula [O],

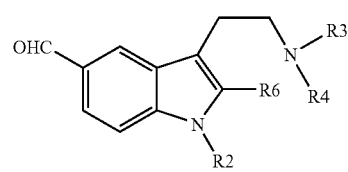

[O]

wherein each of R2, R3, R4 and R$^6$ is as defined above, or a salt thereof, either under simultaneous reduction by means of reductive amination, leading directly to a corresponding compound of the formula [B], or by first reacting with the hydrazine and then subsequent reduction of the resulting hydrazone of the formula [D] as shown above, wherein R, R2, R3, R4 and R6 are as defined above, with a hydrazine of the formula

[F] as defined above wherein R is as defined for formula [B], or a salt thereof, to a compound of the formula [B] as defined above, or a salt thereof, where the compound of the formula [O]] as defined above wherein $R^6$ is a hydrogen, or a salt thereof, is preferably obtained from a compound of the formula [G]] as defined above, wherein L is preferably halogen, especially iodo or bromo, or a salt thereof, by reacting it with first a lithium alkyl compound to form the lithio derivative and then with DMF or triethyl formate, to obtain a corresponding compound of the formula [O], or a salt thereof after hydrolysis.

In an important aspect, the invention relates to a compound of the formula [B] as shown above, or a salt thereof. In the compound of formula [B] and in its precursor of formula [D], R is acyl, preferably lower alkanoyl, such as formyl or acetyl or hydrogen, R2 is a protecting group or preferably hydrogen, and each of R3 and R4 is hydrogen or preferably lower alkyl, more preferably methyl.

Further embodiments of the invention relate to the use of a compound of the formula [E] as defined above, wherein R2 is a protecting group or hydrogen and each of R3 and R4 is hydrogen or preferably lower alkyl, more preferably methyl, or a salt thereof; or to the use of a compound of the formula [H] as defined above, or a salt thereof, wherein R2 is a protecting group or hydrogen, L is halogen, unsubstituted or substituted alkanesulfonyloxy or arylsulfonyloxy, and each of R3 and R4 is hydrogen, preferably lower alkyl, more preferably methyl, in a process for preparing Rizatriptan.

If residue R6 is COOR7 as defined above, the products of formula [A] are obtained from corresponding 2-carboxy derivatives after an additional decarboxylation step at any stage during the proceedings, i.e. after decarboxylation on the stage corresponding to any of formulae [O], [D] or [B], or of formula [A']:

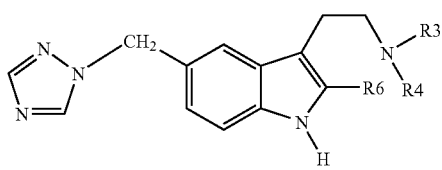

[A']

Residue R7 is hydrogen, one equivalent of a cation, especially an alkali metal cation such as sodium, potassium, or a suitable hydrocarbon residue such as alkyl or substituted alkyl, especially lower alkyl such as $C_1$-$C_4$-alkyl.

Removing the group COOR7 by decarboxylation with formation of the corresponding compound wherein R6 is hydrogen may be effected following methods known in the art, e.g. by heating the carboxylic acid in quinoline in the presence of a copper salt.

Thus, the present invention in one aspect also provides a process for the manufacture of a compound of the formula [D]

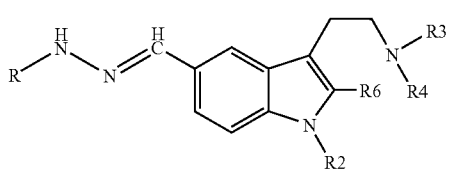

[D]

or a salt thereof, comprising reacting an aldehyde of the formula [O],

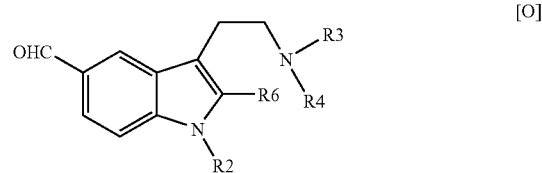

[O]

or a salt thereof, with a hydrazine of the formula [F]

R—NH—NH$_2$      [F]

wherein R6 is hydrogen or COOR7, and each of R, R2, R3, R4 and R7 in the compounds mentioned is as defined above, and if R6 is COOR7 optionally converting COOR7 into hydrogen.

The present invention in another aspect also provides a process for the manufacture of a compound of the formula [B] as defined above, or a salt thereof, comprising reacting an aldehyde of the formula [O],

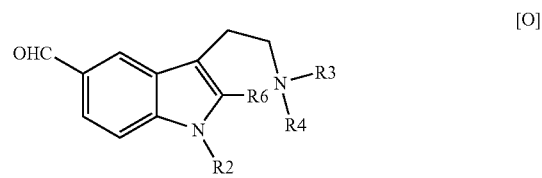

[O]

or a salt thereof, with a hydrazine [F]

R—NH—NH$_2$      [F]

wherein R6 is as defined above, and then subsequent reduction of the resulting hydrazone of the formula [D],

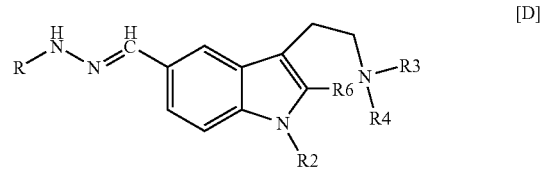

[D]

or salt thereof, to a compound of the formula [B], or a salt thereof, wherein R6 is hydrogen or COOR7, and each of R, R2, R3, R4 and R7 in the compounds mentioned is as defined above and, if R6 is COOR7 optionally converting R6 into hydrogen.

Preferably, if in the compound of formula [O] as defined above R6 is COOR7, prior to the reaction with the hydrazine, R6 is converted into hydrogen, and the compound of the formula [O] is converted into an acid addition salt with a protic acid selected from hydrogen halide, sulphuric or sulphonic acid or a carboxylic acid, which is purified by crystallization or recrystallization.

Unless otherwise indicated, the general terms and names used in the description of the present invention preferably have the following meanings (where more specific definitions, in each case separately, or in combination, may be used to replace more general terms in order to define more preferred embodiments of the invention):

Where compounds or a compound are mentioned, this means these compounds or salts thereof, e.g., where in the compounds acidic groups (e.g. carboxyl or sulfonyl) are present, salts with bases, such as alkali metal salts or ammonium salts, where basic groups (e.g. amino, imino, hydrazine) are present, acid addition salts, e.g. with inorganic acids, such as chlorides or sulfates, or with organic acids, e.g. sulfonic or carbonic acids, such as methane sulfonates, benzoates, oxalates or acetates, where appropriate and expedient. Where both acidic and basic groups are present, also internal salts may be formed. Salts of compounds of the formula [A] are preferably pharmaceutically acceptable salts, while for the purposes of isolation or purification especially of the salts of other compounds mentioned above and below it is also possible to use pharmaceutically unsuitable salts, for example picrates or perchlorates. Only the pharmaceutically acceptable salts or the free compounds (optionally in the form of pharmaceutically compositions) of the compounds of formula [A] are used therapeutically and they are therefore preferred, e.g. benzoate or hydrogen sulfate.

The term "lower" defines a moiety with up to and including maximally 7, especially up to and including maximally 4, carbon atoms, said moiety being branched or straight-chained. Lower alkyl, for example, is methyl, ethyl, n-propyl, sec-propyl, n-butyl, isobutyl, sec-butyl, tert-butyl, n-pentyl, n-hexyl or n-heptyl, or preferably methyl. Lower alkanoyl is preferably acetyl or especially formyl.

In "un-substituted or substituted", "substituted", wherever used for a moiety, means that one or more hydrogen atoms in the respective molecule, especially up to 5, more especially up to three, of the hydrogen atoms are replaced by the corresponding number of substituents which preferably are independently selected from the group consisting of alkyl, especially lower alkyl, for example methyl, ethyl or propyl, hydroxy, mercapto, nitro, cyano, halo, halo-lower alkyl, for example trifluoromethyl, $C_6$-$C_{16}$-aryl, especially phenyl or naphthyl (where $C_6$-$C_{16}$-aryl, especially phenyl or napthyl, is unsubstituted or substituted by one or more, especially up to three moieties selected from N,N-di-lower alkylamino, N-phenyl-lower alkyl-amino, N,N-bis(phenyl-lower alkyl)-amino, and halo-lower alkyl, e.g. trifluoromethyl), $C_3$-$C_{10}$-cycloalkyl, lower alkoxy, for example methoxy, aryl-lower alkoxy, e.g. phenyl-lower alkoxy, lower alkanoyloxy, N,N-di-lower alkylamino, N-phenyl-lower alkylamino, N,N-bis(phenyl-lower alkyl)-amino, di-lower alkylamino, unsubstituted or lower alkyl substituted and/or mono- or di-oxosubstituted heterocyclylenyl or heterocyclyl, e.g. unsubstituted or lower alkyl substituted-imidazolidin-2,4-dionenyl or imidazolidin-2,4-dionyl. It goes without saying that substituents are only at positions where they are chemically possible, the person skilled in the art being able to decide (either experimentally or theoretically) without inappropriate effort which substitutions are possible and which are not.

Acyl is preferably a linear, branched, cyclic, cyclic-linear, saturated or partially or totally unsaturated organic carboxylic acid radical, especially unsubstituted or substituted alkoxycarbonyl, unsubstituted or substituted aryloxycarbonyl, unsubstituted or substituted aryl-lower alkoxycarbonyl, or preferably aryl-carbonyl, aryl-lower alkylcarbonyl or (unsubstituted or substituted alkyl)-carbonyl wherein aryl, alkyl and the substituents if present are preferably as defined above. Preferred is lower alkanoyl, especially acetyl or more especially formyl, or lower alkoxycarbonyl or phenylalkoxycarbonyl such as benzyloxycarbonyl, butyloxycarbonyl, propyloxycarbonyl, ethoxycarbonyl or especially methoxycarbonyl. Most preferred is formyl.

In unsubstituted or substituted alkyl, alkyl preferably has up to 20, more preferably up to 12 carbon atoms and is linear or branched one or more times; preferred is lower alkyl, especially $C_1$-$C_4$-alkyl. Substituted alkyl is especially lower alkanoyoxy-lower alkyl, such as acetoxymethyl, aryl-lower alkyl, especially benzyl, or lower alkanoyloxy-lower alkyl, e.g. acetoxymethyl.

Aryl is unsubstituted or substituted, and preferably has a ring system of not more than 24 carbon atoms, especially not more than 16 carbon atoms, is preferably mono-, bi- or tricyclic, and is unsubstituted or substituted preferably as defined above under "Substituted"; for example, aryl is selected from phenyl, naphthyl, indenyl, azulenyl and anthryl, and is preferably in each case unsubstituted or substituted phenyl. Unsubstituted aryl, preferably phenyl, is especially preferred.

In unsubstituted or substituted alkanesulfonyloxy, unsubstituted or substituted alkyl is preferably as defined above; preferred is unsubstituted or halogen substituted lower alkanesulfonyloxy, such as methanesulfonyloxy or trifluormethylsulfonyloxy.

In arylsulfonyloxy, aryl which can be unsubstituted or substituted is preferably as defined above, e.g. lower-alkyl substituted phenyl; preferred is toluolsulfonyloxy.

Halogen or halo is preferably fluoro, chloro, bromo or iodo, most preferably chloro; bromo or iodo (if not stated otherwise).

Protecting groups, especially R2, especially for derivatising amino groups as in the case of R2, are generally known in sugar, amino acid and nucleotide chemistry, and they as well as methods for their introduction as well as their removal are described, for example, in standard text books (see J. F. W. McOmie, "Protective Groups in Organic Chemistry", Plenum Press, London and New York 1973; Th. W. Greene, "Protective Groups in Organic Synthesis", Wiley, New York 1981, in "The Peptides", Volume 3 (E. Gross and J. Meienhofer, eds.), Academic Press, London and New York 1981; "Methoden der organischen Chemie", Houben-Weyl, 4th edition, Volume 15/1, Georg Thieme Verlag, Stuttgart 1974; and H.-D. Jakubke and H. Jescheit, "Aminosäuren, Peptide, Proteine" ("Amino acids, peptides, proteins"), Verlag Chemie, Weinheim, Deerfield Beach and Basle 1982), which are incorporated by reference herein regarding these protecting groups, their introduction and/or their removal.

An R2-protected imino group may be protected, for example, by acyl (which can be removed e.g. by hydrolysis or reduction), arylmethyl (which can be removed by catalytic hydrogenation or reduction in the presence of hydrazine or sodium hypophospite or the like), unsubstituted or substituted lower alkyl, unsubstituted or substituted alkoxymethyl, etherified mercapto, 2-acyl-lower alk-1-enyl, silyl, in the form of an N-lower alkylpyrrolidinylidene group or in the form of an azido group, or as substituted-sulfonyl amino, N,N-di-alkylformamidinyl (which can be removed e.g. with acid, such as HCl, or base, e.g. KOH), vinyl or allylamino. Preferred imino- and amino-protecting groups are lower alkoxycarbonyl, phenyl-lower alkoxycarbonyl, fluorenyl-lower alkoxycarbonyl, 2-lower alkanoyl-lower alk-1-en-2-yl and lower alkoxycarbonyl-lower alk-1-en-2-yl, with most preference being given to isobutyryl, benzyl, p-methoxybenzyl, 3,4-dimethoxybenzyl, 3-methoxybenzyl, 2-nitrobenzyl, 2,4-dinitrophenyl, phenacyl, triphenylmethyl, benzoyl, tert-butoxycarbonyl, benzyloxycarbonyl, N-2-chloroethyl, N-(1-ethoxy)ethyl, tri-lower alkylsilyl, N-phenoxyacetyl, trichloroethyloxycarbonyl, cyclohexyl-oxycarbonyl, 1- or 2-adamantyl-oxycarbonyl, 4-tert-butylphenoxyacetyl, methoxymethyl, diethoxymethyl, chloroethoxymethyl, N,N-dimethylformamidinyl, mesitylenesulfonyl, p-methoxysulfonyl, benzenesulfonyl or N-methylpyrrolidin-2-ylidene, or the like.

It should be mentioned that also in other cases of reactions of the present inventions functional groups the participation of which in reactions is to be suppressed can be protected and deprotected at appropriate stages as required and/or desirable.

Where desired or necessary, compounds from intermediate reactions or the final reaction leading to the compound of the formula [A], or a salt thereof, can be purified or obtained in pure form according to standard procedures, such as evaporation, filtration, crystallization, chromatography, drying, extraction, acidification, alkalinization, centrifugation and the like.

Where necessary or desirable, reactions are conducted under an inert gas such as argon or nitrogen, and/or absolute solvents are used. Where elevated pressures are applied, the reaction, where required, takes place in a pressure vessel.

Where references (e.g. patent applications, patents or publications in journals) are mentioned hereinbefore and hereinafter, their content with respect to the reactions or compounds mentioned, respectively, are included by reference into the present disclosure.

Where a solvent or solvents are mentioned, this is intended to include also mixtures of solvents. Where not indicated that certain solvents are to be used, solvents may, for example, be selected from the following: The solvents from which those solvents that are suitable for any particular reaction may be selected include, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, carboxylic acid anhydrides, such as lower alkanoic acid anhydrides, for example acetic anhydride, cyclic, linear or branched hydrocarbons, such as cyclohexane, hexane or isopentane, or mixtures of solvents, for example aqueous solutions, unless otherwise indicated in the description of the processes. Such solvent mixtures may also be used in working up, for example by chromatography or partitioning.

1,2,4-Triazolyl forming reagents are especially those that form with the R—NH—NH in 5-position of the indole ring in formula [B] a 5-(1,2,4-triazol-1-yl) moiety, with those in the following paragraph mentioned "as 1,2,4-triazolyl forming reagent" being preferred:

In the reaction of a compound [B] or a salt thereof to a compound of the formula [A] (especially Rizatriptan), or a salt thereof, the triazole ring formation (cyclisation) is preferably accomplished either (i) with Gold's reagent {[3-(dimethylamino)-2-azaprop-2-en-1-ylidene]-dimethylammonium chloride} as 1,2,4-triazolyl forming reagent, which is preferably used in equimolar or higher amounts related to the compound of the formula [B] or its salt, preferably in the presence of an appropriate solvent, such as a hydrocarbon, an ester or preferably a halogenated (especially chlorinated) hydrocarbon, such methylene chloride or trichloromethane, preferably at elevated temperatures, such as between 30° C. and reflux temperature of the reaction mixture, preferably under an inert gas such as nitrogen (for appropriate reaction conditions see e.g. Jenkins et al, J. Med. Chem. 35(13), 1992, 2392-2406, or U.S. Pat. No. 4,556,717); or (ii) with 1,3,5-triazine as 1,2,4-triazolyl forming reagent, preferably in a 0.1- to 3-fold molar relationship to the compound of the formula [B], preferably in a (more preferably absolute) polar solvent, such as nitriles (e.g. acetonitrile) or alcohols, e.g. a lower alkanol, advantageously methanol or preferably ethanol, preferably at elevated temperatures, such as 30° C. to the reflux temperature of the reaction mixture (for appropriate reaction conditions see e.g. Grundmann et al., J. Org. Chem. 21, 1956, 1037-1038, or U.S. Pat. No. 4,556,717); or (iii) with formamidine or preferably a formamidinium salt (e.g. the acetate or chloride) as 1,2,4-triazolyl forming reagent, preferably in more than equimolar amounts related to the compound of the formula [B], preferably in a polar solvent, e.g. a nitrile, such as acetonitrile, preferably at elevated temperatures, e.g. between 30° C. and the reflux temperature of the reaction mixture (for appropriate reaction conditions see e.g. Chem. Ber. 114, 1981, 2825-2833, and/or U.S. Pat. No. 4,556,717); or (iv) with formamide, see especially U.S. Pat. No. 4,556,717 which is incorporated by reference here with regard to this type of reaction, or (v) any appropriate combination of two or more of the mentioned reaction conditions.

Where, prior to the ring formation with the 1,2,4-triazolyl forming reagent(s), removal of R acyl is required, this is effected by standard hydrolysis procedures (preferred; e.g. in the presence of acid or preferably of base, e.g. alkaline metal hydroxide, such as sodium and/or potassium hydroxide, e.g. to remove R2=acetyl or formyl) or further by catalytic hydrogenation, the latter preferably being directly effected when a compound of the formula [D], or a salt thereof, and/or a compound of the formula [E], or a salt thereof, each with R=acyl, is reacted under reductive conditions to the compound of the formula [B], or a salt thereof, as described above or in more detail below, so that a combination of these reaction steps forms an advantageous embodiment of the present invention.

Where desired, the conversion of salts into different salts, or of free compounds into the salts, of compounds of the formula [A] (or any other educts and intermediates for its synthesis) takes place in customary manner, for example by treatment with a suitable acidic agent or an ion exchange resin. Also the conversion of salts into the free compounds takes place according to standard conditions, where desired.

The reaction of a compound of the formula [D] to a compound of the formula [B] (or salts thereof, respectively) under reductive conditions preferably takes place in the presence of hydrogen and a (preferably heterogeneous) catalyst, e.g. a Raney metal catalyst, preferably Raney-Ni or Raney-Co, or a noble metal on a carrier, e.g. Palladium on charcoal (Pd/C), Rhodium on charcoal (Rh/C), Platinum on charcoal (Pt/C) or Ruthenium on charcoal (Ru/C), more preferably Palladium on charcoal (Pd/C); in an appropriate solvent, such as an alcohol, e.g. a lower alkanol, such as methanol or ethanol, and/or an ester, such as a lower alkanoyl lower alkanoate, e.g. ethylacetate, in the absence or presence of water, preferably under elevated pressure (e.g. 2 to 200, preferably 30 to 80 bar hydrogen pressure), at customary temperatures, e.g. between 0 and 80° C., e.g. at ambient (especially room) temperature. Appropriate conditions for the reduction are known (see e.g. U.S. Pat. No. 4,557,717).

The reaction of the compound of the formula [D], or a salt thereof, to compound [A], or a salt thereof, can be led separately (e.g. in the case where the compound of the formula [D] is made from an aldehyde of the formula [O] as described above and particularly below, this combination of reactions thus forming a particularly advantageous embodiment of the present invention), or it can take place as single step after or directly in combination (e.g. as one-pot reaction) with the reaction of a compound of the formulae [E] and [F] (or salts thereof, respectively), as described above and in particular below, so that this combination or the sequential reactions [E]+[F]->[D]->[B], especially further to [A], form a very advantageous embodiment of the present invention. The reaction conditions are preferably those described above for the reaction of a compound of the formula [D] to a compound of the formula [B][, with Pt/charcoal being less preferred as catalyst. For the conditions of conversion of a cyanide into a hydrazine those mentioned in U.S. Pat. No. 4,556,717 are a useful example.

Also the separate reaction of [E] with [F] to [D] under reductive conditions preferably takes place with hydrogen under the reaction conditions mentioned above for the reaction of a compound of the formula [D] to a compound of the formula [B], with Pt/charcoal being less preferred as catalyst. As example preferably the conditions of conversion of a cyanide into a hydrazine mentioned in U.S. Pat. No. 4,556,717 can be employed by way of analogy.

In the reaction of a compound of the formula [G], or a salt thereof, to a compound of the formula [E] with a cyanide salt, where preferably L is bromo or especially iodo, the cyanide salt is preferably a metal cyanide, especially selected from the group consisting of zinc cyanide ($Zn(CN)_2$) in the presence of a catalyst such as $Pd(dppf)Cl_2$, an alkyli metal cyanide in the presence of a Ni(O)-ccomplex, such as $Ni(PPh_3)$ which is preferably generated in situ from $Ni(PPh_3)Cl_2$ by reduction with an additional metal such as manganese or zinc, see Bull. Chem. Soc. Jpn. 1988, 61, 1985, or preferably Copper(I) cyanide in NMP (N-methyl-pyrrolidone), where the Copper (I)cyanide is preferably used a molar excess, e.g. 1.1 to 2, for example about 1.5 equivalents; at a preferred temperature in the range from 100 to 220° C., e.g. from 180 to 200° C.

Alternatively, a compound of the formula [E] can also be obtained in accordance with the methods described in U.S. Pat. No. 5,510,359

In the reduction of a compound of the formula [H] to a compound of the formula [G], or a salt thereof, or of a compound of the formula [C] to a corresponding compound of the formula [B] in the presence of borane, the borane is preferably obtained in situ from an alkali metal borohydride, especially sodium borohydride, in the presence a lewis acid, especially a boron trihalogenide etherate, such as the boron trifluoride etherate with diethyl ether, and the reaction preferably takes place in an appropriate solvent, e.g. en ether, for example a di-lower alkoxy lower alkane, such as dimethoxy-ethane, ethyleneglycol dimethyl ether or a cyclic ether, e.g. tetrahydrofurane, at preferred temperatures in the range from −20 to 50° C., especially between −15 to 30° C.; the following reaction subjecting the resulting product(s) to removal of borane from any amino borane intermediates (which can preferably follow without isolation of the borane carrying intermediates, that is, as one-pot reaction, preferably after addition of a metal salt base, e.g. an alkali metal hydroxide in water, such as sodium or potassium hydroxide)) preferably takes place to an appropriate acceptor of the borane moiety or moieties to be removed, e.g. an amine, preferably with DABCO (diazabicyclo[2.2.0]octane) in an appropriate solvent, e.g. as just mentioned, where water may also be present if a metal salt base has been added, and preferably at elevated temperatures, e.g. between 50° C. and reflux temperature, for example at about 80° C., and the subsequent oxidation/de-hydrogenation with an oxidant such as a quinone or, advantageously, manganese dioxide (which is preferably conducted after partial isolation of the resulting product with some extraction steps) is preferably conducted in an appropriate solvent, e.g. an ether, such as a di-lower alkylether, e.g. tert.-butyl-methyl ether, preferably at temperatures between 10° C. and reflux temperature, e.g. between 20 and 50° C.

The reaction of a compound of the formula [I] to a compound of the formula [H] with an electrophile capable of introducing group L, especially halogen by reaction with a halo-succinimide, especially N-chloro succinimide used to introduce chloro, preferably takes place in an appropriate solvent, e.g. a lower alkanoic acid, e.g. acetic acid, or a halogenated hydrocarbon, e.g. dichloroethane, and/or an aromatic solvent, e.g. chlorobenzene, a customary temperatures, e.g. from 10 to 40, such as from 20 to 30° C.

The reaction of a compound of the formula [K] with a compound of the formula [L] (an active carbonic acid derivative wherein X is preferably chloro or bromo), to a compound of the formula [I] preferably takes place in the presence of a tertiary nitrogen base, preferably in an appropriate solvent, e.g. an ester, e.g. a cyclic ester, such as tetrahydrofurane, or preferably a lower alkyl-lower alkanoate, such as ethyl acetate, more preferably in the presence also of a N,N-di-(lower alkyl)-lower alkanoylamide, a lower alkanol, e.g. methanol or ethanol, or a di-lower alkylsulfoxide, e.g. dimethylsulfoxide, especially of N,N-dimethyl formamide (especially where one-pot synthesis from [M] via [K] to [I] is used, see below), preferably at temperatures from 10° C. to the reflux temperature or the reaction mixture, e.g. from 20 to 65° C.

The reaction of a compound of the formula [M] to a compound of the formula [K] with malonic acid in the presence of a pyridine, especially pyridine (very preferred) and/or one or more picolines, in the absence or presence of a N,N-di-(lower alkyl)-lower alkanoylamide (preferred), a lower alkanol, e.g. methanol or ethanol, or a di-lower alkylsulfoxide, e.g. dimethylsulfoxide, especially of N,N-dimethyl formamide, advantageously takes place in the presence of an ester, preferably a lower alkyl alkanoate, more preferably ethyl acetate, as a cosolvent, preferably at temperatures between 30° C. and reflux temperature, e.g. between 50 and 90° C., for example between 60 and 80° C., and is followed by conversion of the resulting compound which is present as a salt of a pyridine into the salt of the base NB given in formula [K], preferably by addition of the base NB to the reaction mixture (which in addition may also serve the reaction with a compound of the formula [L] in a subsequent reaction to produce a compound of the formula [I]) where the reaction of the isatine compound of the formula [M] and the conversion of the product salt of a pyridine into the corresponding salt of the formula [K] and more preferably also the reaction to give the compound of the formula [I] by reaction with a compound of the formula [L] preferably take place in the same reaction vessel.

A tertiary nitrogen base NB where the nitrogen is not part of a ring is preferably a nitrogen substituted by three moieties selected from alkyl, such as lower alkyl, especially ethyl, $C_3$-$C_7$-cycloalkyl, such as cyclohexyl, or phenyl-lower alkyl, such as benzyl. Preferred as base NB are N,N-dicyclohexyl-N-lower alkylamines, such as dicyclohexyl-ethylamine, or especially tri-lower alkylamines, such as triethylamine.

In the preferred alternative for synthesis of a compound of the formula [H], the reaction of a compound of the formula [K*] with a compound of the formula [L] to a corresponding compound of the formula [H] takes place under the conditions just described for reaction of a compound of the formula [K] with a compound of the formula [L] to a compound of the formula [I].

Also the reaction of a compound of the formula [M*] to a compound of the formula [K*], as well as the salt conversion, preferably takes place under the same conditions as just described for the synthesis of a compound of the formula [K] from a compound of formula [M]. Also here, the reaction of the isatine compound of the formula [M*] and the conversion of the product salt of a pyridine into the corresponding salt of the formula [K*] and more preferably also the subsequent reaction to give the compound of the formula [I] by reaction with a compound of the formula [L] preferably take place in the same reaction vessel.

Alternatively, a compound of the formula [B], or a salt thereof, can be obtained starting from a compound of the formula [C]—the reaction conditions are preferably the same as described above for the conversion of a compound of the formula [H] to a compound of the formula [G].

The reaction of a compound of the formula [N] with a compound of the formula [F] (preferably with R=H) to a compound of the formula [C] preferably takes place under standard conditions for the hydrazinolysis of carbonic esters, e.g. in the presence of an appropriate solvent, such as an alcohol, e.g. a lower alkanol such as methanol, ethanol or isopropanol, preferably at elevated temperatures, e.g. between 50° C. and the reflux temperature of the reaction mixture, where preferably 0.5 to 5 equivalents of the hydrazine compound of the formula [F] is used in relationship to the compound of the formula [N].

The reaction of a compound of the formula [H] with carbon monoxide in the presence of the corresponding alcohol R5-OH, preferably wherein R5 is lower alkyl, e.g. ethyl or methyl, or benzyl, to a corresponding compound of the formula [N] takes place in the presence of a catalyst, preferably a homogenous Pd catalyst, e.g. Pf(dppp)Cl$_2$, and a tertiary nitrogen base, e.g. a tri-lower alkylamine, such as triethylamine, preferably in a polar solvent, e.g. an alcohol, such as ethanol, preferably takes place under elevated CO pressure, e.g. between 10 to 50 bar, preferably at elevated temperatures, e.g. from 40 to 150° C., for example between 100 and 130° C.

The reaction of an aldehyde of the formula [O], or a salt thereof, to a compound of the formula [B], or a salt thereof, with a hydrazine of the formula [F] can be conducted either under simultaneous reduction by way of reductive amination directly to a corresponding compound of the formula [B], or by first reacting with the hydrazine and then subsequent reduction of the resulting hydrazone of the formula [D]; the conditions are in each case standard conditions, for example, the reaction with simultaneous reduction (by reductive amination) preferably takes place under catalytic hydrogenation, e.g. with hydrogen in the presence of a heterogeneous catalyst, such as a Raney-metal, e.g. Raney-Ni or Raney-Co, or a transition metal catalyst on a carrier, such as carbon, e.g. Pd/C, Ru/C, Rh/C or Pt/C, in an appropriate solvent, e.g. an alcohol, such as a lower alkanol, for example methanol or ethanol, preferably under pressure up to 15 MPa, preferably at temperatures from 5 to 100° C.; while in the reaction with sequential formation of a hydrazone of the formula [B] by first reacting with the hydrazine of the formula [F] to a corresponding hydrazone compound of the formula [D] that is then reduced to a compound of the formula [B], preferably the hydrazone is first formed by reaction of [O] and [F] (or salts thereof where present) in the presence of an appropriate solvent, e.g. an aromatic solvent, such as toluene, or a polar solvent, e.g. an alcohol, such as a lower alkanol, e.g. methanol or ethanol, in the presence or absence of water, where required in the presence of an acid as catalyst, e.g. sulphuric acid, p-toluene sulfonic acid or formic acid, at preferred temperatures from 10° C. to the reflux temperature of the reaction mixture; subsequently, with or without partial or complete isolation, the resulting compound of the formula [D], or its salt, is then reduced by catalytic hydrogenation as just described, or alternatively with sodium borohydride, e.g. under the conditions described in *Carbohydr. Res.* 2000, 327 (4), 463 which, in this regard, is incorporated by reference here.

The reaction of a compound of formula [G] wherein L is halogen, especially iodo or bromo, or a salt thereof to a compound formula [O] wherein residue R6 is hydrogen, by reacting it with first a lithium alkyl compound to form the lithio derivative and then with DMF (N,N-dimethyl formamide) or triethyl formate, plus hydrolysis to [O], preferably is accomplished under the following conditions: The lithiation may, for example, be performed in an ether solvent at a temperature from initially −70 to −30° C. to finally −10° C., using, for example, tert-butyl-Li; preferably it is performed in an apolar solvent such as an ether, a hydrocarbon or an aromatic solvent such as toluene (more preferred) alone or also in the presence of an amine such as triethylamine or N,N'-tetramethylethylenediamine, especially in the range −30 to +40° C., using, for example, n-alkyl Li such as butyl-Li or hexyl-Li. The lithiated species is then reacted with N,N-dimethyl formamide (DMF), or triethyl orthoformate within a preferred temperature range from −20 to 60° C. Hydrolysis of the intermediate product is preferably performed in a temperature range from 0-100° C., more preferably in the range from 20-80° C. A further variant to obtain a compound of the formula [O] is described in U.S. Pat. No. 5,510,359.

R2=acyl can be introduced in any compound with a indole nitrogen in 1-position of the indole ring system mentioned hereinbefore and hereinafter at every appropriate stage, e.g. by reaction with a symmetric acid anhydride of the acid forming the basis for an acyl group R2 or a mixed anhydride, preferably an anhydride of an alkanoic acid, in the presence or absence of a further solvent, at elevated temperatures, especially under reflux.

Starting materials or reagents for which the synthesis is not mentioned explicitly in the present disclosure (such as compounds of the formula [F], or salts thereof) are commercially available, prepared according to standard methods or known in the art.

Where compounds (or salts thereof) are mentioned above as embodiments of the invention, these are especially important as intermediates for the synthesis of compounds of the formula [A], or salts thereof, and thus for the synthesis of tryptophanes or related compounds.

Where educts or intermediates are used, the products of their reaction are, regarding their moieties, corresponding to the used intermediates or educts, if not indicated otherwise.

PREFERRED EMBODIMENTS OF THE INVENTION

The invention relates to the single reaction steps as given above or below, as well as any combination of two or more reaction sequence steps that are in succession, that is, where the product of one reaction is the precursor of the next reaction that is part of such combination.

Where subsequently formulae are mentioned, this is intended to refer to the formulae given above, respectively.

Especially preferred is the combination of the reaction of a compound of the formula [D] to a compound of the formula [B] that is then reacted to a compound of the formula [A] as described above or below, where preferably the compound of the formula [D] is produced by reaction of a compound of the formula [E] with an compound of the formula [F], where preferably the compound of the formula [E] is obtained by reaction of a compound of the formula [G], which is preferably obtained from a compound of the formula [H], which is preferably obtained either (a) from a compound of the formula [I] that is preferably obtained from a compound of the formula [K] by reaction with a compound of the formula [L], where the compound of the formula [K] is preferably obtained from a compound of the formula [M]; or (ii) from a compound of the formula [K*] by reaction with a compound of the formula [L], where the compound of the formula [K*] is preferably obtained from a compound of the formula [M*]; in each case preferably under the (especially the more preferred) reaction conditions described above or below; where for each compound, where salt-forming groups are present, the free compound or a salt thereof may be used or produced.

Alternatively, especially preferred is the combination of the reaction of a compound of the formula [C] to a compound of the formula [B] that is then reacted to a compound of the formula [A] as described above or below, where preferably the compound of the formula [C] is produced by reaction of a compound of the formula [N] with a compound of the formula [F], where preferably the compound of the formula [N] is obtained from a compound of the formula [H] which is preferably produced by one of the two ways described in the last paragraph; in each case preferably under the (especially the more preferred) reaction conditions described above or below; where for each compound, where salt-forming groups are present, the free compound or a salt thereof may be used or produced.

In still another preferred way, the combination of the reaction of a compound of the formula [O] with a compound of the formula [F] to a compound of the formula [D] that is then reacted to a compound of the formula [A] as described above or below is preferred; in each case preferably under the (especially the more preferred) reaction conditions described above or below; where for each compound, where salt-forming groups are present, the free compound or a salt thereof may be used or produced.

In an especially preferred route, rizatriptan, or a pharmaceutically relevant salt thereof such as rizatriptan benzoate, is prepared according to the following scheme:

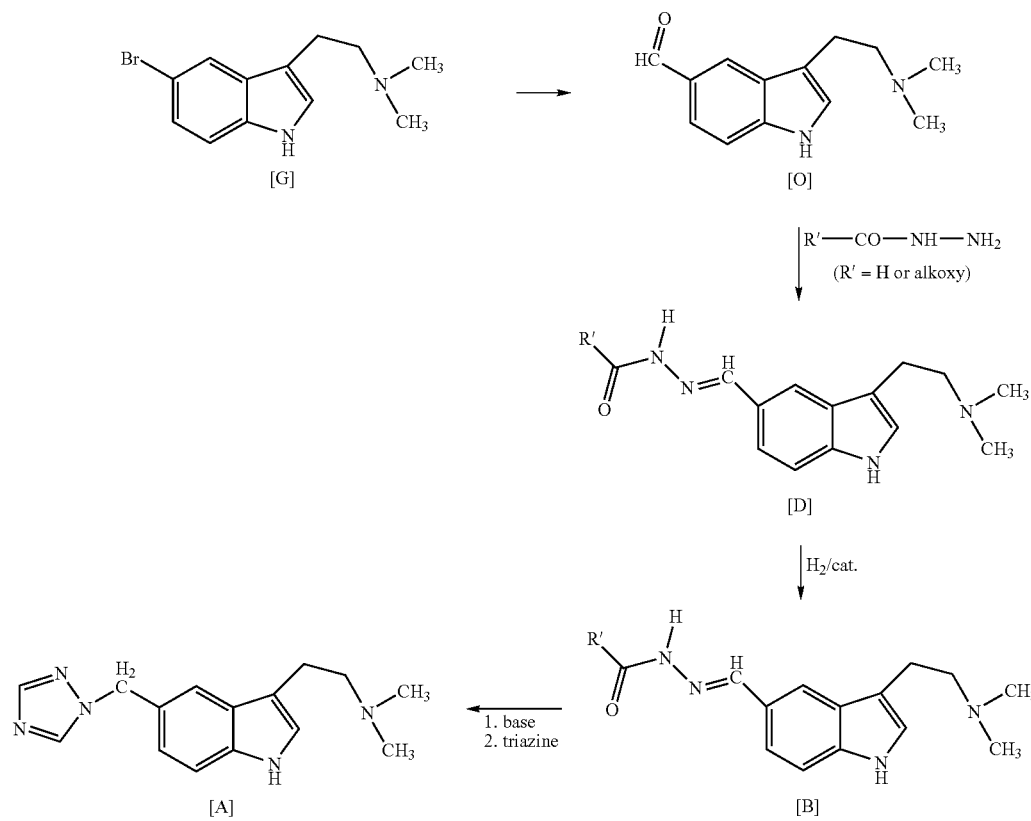

One or more purification steps are advantageously introduced into the preparation route, preferably by crystallization of the intermediate from a suitable solvent and optional recrystallization. In the preferred route via aldehyde of the formula [O], this type of intermediate purification may be achieved using the intermediate on the stage of formulae [O], [D] and/or [B] in the form either as depicted by the molecular formula or as an acid addition salt, e.g. a pharmaceutically acceptable salt as described further above. Solvents are preferably selected from class 3 solvents (classification by the U.S. food and drug administration); in case of acidic solvents, these may the same time be used for obtaining an acid addition salt. Preferred solvents include water, lower alkyl alcohols, esters, ketones, sulfoxides, ethers, or suitable alkanes, or mixtures of these solvents.

Of special technical importance is the purification of the aldehyde of formula [O] or its 1:1 acid addition salt e.g. with a hydrogen halogenide, sulfuric or sulfonic acid or a carboxylic acid, preferably the hydrochloride or monooxalate. Preferred is the recrystallization from toluene, a $C_5$-$C_8$alkane, dimethylsulfoxide, lower alkanol, lower alkyl ether, or mixtures thereof, especially of its the 1:1 addition salt with oxalic acid in alcohol such as ethanol and/or ether such as diethyl ether.

A purification step may also be introduced on the stage of formula [D], e.g. isolation of the intermediate by crystallization. This is preferably achieved with a compound of formula [D] wherein R is formyl or lower alkoxycarbonyl such as CH₃OCO; most preferably by crystallization of a compound of the formula [D] wherein R is formyl, or by crystallization of an acid addition salt of the compound of the formula [D] wherein R is lower alkoxycarbonyl. Suitable acid addition salts include salts of protic acids such as hydrochlorides or hydrobromides. Preferred is the crystallization with optional recrystallization of the plain hydrazone [D] or its monohydrochloride.

The compound of the formula [B], especially wherein R is formyl or lower alkoxycarbonyl such as CH₃OCO, is preferably crystallized or recrystallized before conversion to the compound of formula [A]. This is advantageously achieved with a mono- or especially diammonium salt thereof (addition salt with 1 or 2 equivalents of a protic acid), e.g. the mono- or dihydrochloride of the compound of the formula [B].

The invention also relates especially to the following intermediates in the synthesis of a compound of the formula [A], or precursors therefore:

A compound of the formula [B], wherein R is lower alkanoyl, especially lower alkoxycarbonyl or acetyl, or preferably formyl or hydrogen, R2 is hydrogen and each of R3 and R4 is methyl, or a salt thereof;

a compound of the formula [C], wherein R is lower alkanoyl, especially lower alkoxycarbonyl or acetyl, or preferably formyl or hydrogen, R2 is hydrogen and each of R3 and R4 is methyl, or a salt thereof;

a compound of the formula [D], wherein R is lower alkanoyl, especially lower alkoxycarbonyl or acetyl, or preferably formyl or hydrogen, R2 is hydrogen, and each of R3 and R4 is methyl and R6 is hydrogen, or a salt thereof;

a compound of the formula [G], wherein R2 is hydrogen and each of R3 and R4 is methyl, or (less preferably) a salt thereof;

a 1:1 acid addition salt of the compound of the formula [O] with a hydrogen halogenide, sulfuric or sulfonic acid or a carboxylic acid, preferably the hydrochloride or monooxalate.

Preferred embodiments of the invention can be found in the claims the dependent claims representing preferred embodiments of the invention. In the claims, more general definitions can be replaced with the more specific definitions given above, independently or together with some or all other general expressions used in the same claim, respectively, thus leading to further preferred embodiments of the invention.

Highly preferred embodiments of the invention are those where in the processes mentioned above the formulae represented above are replaced with the corresponding specific compounds mentioned in the examples.

Very preferred process steps, combinations of process steps, novel starting materials and intermediates (compounds) that are part of the present invention are described in the subsequent examples, thus forming very preferred embodiments of the invention.

EXAMPLES

The following examples serve to illustrate the invention without limiting the scope thereof. Wherever ambient temperature or room temperature is mentioned or no temperature is given, this denotes a temperature in the range 20-25° C. Me stands for methyl if not otherwise indicated. Further abbreviations:

THF tetrahydrofuran

DMF dimethylformamide

DMSO dimethylsulfoxide

DME dimethoxyethanol

DABCO diazabicyclo[2.2.2]cyclooctane

TBME tert-butyl methyl ether

HPLC high pressure liquid chromatography

The subsequent Reference Examples are from Ciba Patent Application WO 04056769 (appl. No. PCT/EP03/50992), the examples of which, especially regarding intermediates and final products falling under any of the formulae of the present invention, are here incorporated by reference as reference examples.

Reference Example 1

Preparation of 2-(5-Bromo-3-hydroxy-2-oxo-2,3-dihydro-1H-indol-3-yl)-N,N-dimethyl-acetamide

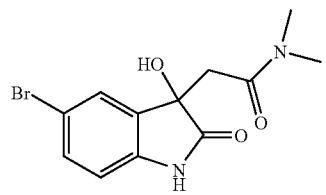

A 2 L flask fitted with an inner thermometer, mechanical stirrer, and reflux condenser is charged with 5-bromo-isatin (100 g, 0.442 mol), malonic acid (55.2 g, 053 mol), pyridine (100.6 g, 1.274 mol), dimethyl formamide (80 g), and ethyl acetate (100 g). When the temperature of the mixture reaches 60° C., the bromo isatin starts to dissolve, and a deep red mixture forms. Carbon dioxide starts to evolve, and after about 45 minutes the precipitation of the intermediate pyridinium (5-bromo-3-hydroxy-2-oxo-2,3-dihydro-1H-indol-3-yl)-acetate starts. The reaction mixture is kept at 80° C. for another 3 hours. Then triethyl amine (49.2 g, 0.486 mol) is added, and the pyridinium salt dissolves to give a deep brown solution. This solution is allowed to cool to 50° C., and then a solution of dimethyl carbamoyl chloride (48 g, 0.442 mol) in 40 g of ethyl acetate is added dropwise during 30 minutes. Carbon dioxide evolves, and the temperature rises to 60° C. After about 45 minutes, the product starts to precipitate from the reaction mixture. The mixture is kept at 60° C. for another hour, and then water (500 mL) and 36% HCl (250 mL, 4 mol) are added in that order during 10 minutes. The product is filtered off, and reslurried in an mixture of acetone/water (500 mL, 1:1, v:v). The slurry is filtered again, and the product is finally dried to give the title compound as a gray powder which is of suitable purity for direct use in the further steps. Yield: 75.2 g (54.2%). An analytically pure sample is obtained by recrystallization from methanol, mp=245-246° C., dec.

Reference Example 2

Preparation of [2-(5-Bromo-1H-indol-3-yl)-ethyl]-dimethyl-amine

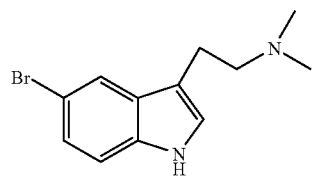

A 1 L flask is charged with 2-(5-bromo-3-hydroxy-2-oxo-2,3-dihydro-1H-indol-3-yl)-N,N-dimethyl-acetamide (Reference Example 1) (31.2 g, 0.1 mol), sodium borohydride (11.8 g 96%, 0.3 mol), and 250 mL of dimethoxyethanol (DME). The mixture is cooled to −15° C., and to the stirred suspension, $BF_3$-etherate (56.6 g, 0.4 mol) is added dropwise. The temperature is maintained between −15 and −10° C. during the exothermic addition. The mixture is then allowed to warm slowly to ambient temperature (25-27° C.), and left stirring over night. The mixture is cooled with an ice bath and quenched by the addition of 4N NaOH (200 mL). The formed viscous emulsion is heated to 80° C. for 30 minutes, then diazabicyclo[2.2.2]cyclooctane (DABCO) (12.7 g 97%, 0.11 mol) is added, and then the mixture is heated for two additional hours under reflux. After cooling to ambient temperature, the aqueous layer is removed and the organic layer is extracted twice with each 50 mL of a 4 N NaOH.solution. After re-extraction of the combined inorganic layers with toluene (150 mL), the aqueous phase is disposed off, and the toluene layer is added back into the reaction vessel. To the vessel, additional toluene (150 mL) is added and the mixture is then extracted with water (200 mL). The aqueous layer is separated, and extracted twice with each 150 mL of toluene. After disposal of the inorganic the combined toluene layers are extracted for three times with water (300 mL, 2×150 mL), and the aqueous layer is again discarded. The toluene layer is then extracted twice with 4N HCl (100 mL and 50 mL). Using the combined acidic extracts, the pH is then adjusted to 14 by the addition of 4 N NaOH. Then the aqueous layer is extracted twice with tert-butyl methyl ether TBME (150 mL and 50 mL), and the combined extracts are washed with brine (50 mL) and then transferred into a 500 mL flask. To the stirred TBME solution, $MnO_2$ (34.8 g, 0.4 mol) is then added, and temporarily the temperature rises to 40° C. After one hour the aniline by-product has been converted completely, and then the $MnO_2$ is filtered off. Removal of the solvent from the filtrate gives the title product as a colourless viscous oil which crystallizes (23.85 g, 85%), mp=95-96° C.

Reference Example 3

Preparation of 3-(2-dimethylamino-ethyl)-1H-indole-5-carbonitrile

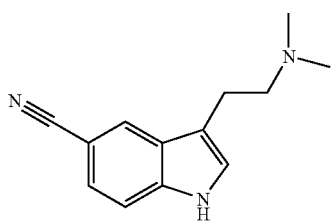

Under an inert atmosphere a flask is charged with [2-(5-bromo-1H-indol-3-yl)-ethyl]-dimethyl-amine (Example 3) (1.0 g, 3.74 mmol), zinc cyanide (0.235 g, 2 mmol), $Pd_2(dba)_3$xCHCl$_3$ (0.194 mg, 5 mol %), dppf (bis-diphenylphosphino ferrocene) (0.207 g, 0.374 mmol, 10 mol %), and DMF (12 mL). The orange slurry is heated to 110° C. and stirred for 21 hours. To the black suspension, which has formed, THF (100 mL) is added, and this is extracted with 1 N NaOH (100 mL). The organic layer is washed with water twice (50 mL each), dried and removal of the solvent gives the title product (0.67 g, 84%) as brown solid.

Reference Example 4

2-(3-Hydroxy-5-iodo-2-oxo-2,3-dihydro-1H-indol-3-yl)-N,N-dimethyl-acetamide

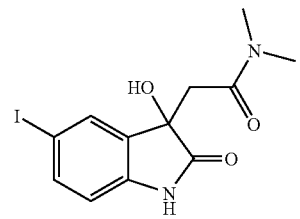

A 2 L flask with mechanical stirrer is charged with 5-iodo-isatin (78.1 g, 0.286 mol), malonic acid (35.7 g, 0.343 mol), and pyridine (90.4 g, 1.144 mol). The mixture is heated to 80° C. When most of the isatine has dissolved, ethyl acetate (100 mL) is added to prevent blocking of the stirrer by the precipitating pyridinium (3-hydroxy-5-iodo-2-oxo-2,3-dihydro-1H-indol-3-yl)-acetate. After 1 hour, precipitation of the latter salt starts, and when the mixture has been kept stirring for another 2 hours, a suspension of the salt in an orange solution has formed. To this is added triethyl amine (43.3 g, 0.429 mol), and the salt dissolves to give a dark solution. Then a solution of dimethyl carbamoyl chloride (40 g, 0.372 mol) in ethyl acetate (50 mL) is added dropwise during 20 minutes. A solid starts to precipitate, and the mixture is stirred for another 2 hours at 80° C. Then 4 N HCl is added (350 mL), and stirring is continued for 30 additional minutes in order to hydrolyze any excess carbamoyl chloride. The mixture is then filtered, and the filter cake is washed with 50% ethanol and then with water. After drying 72.6 g (70.5%) of a grayish powder of the title compound, mp.=246° C.

Reference Example 5

Preparation of [2-(5-Iodo-1H-indol-3-yl)-ethyl]-dimethyl-amine

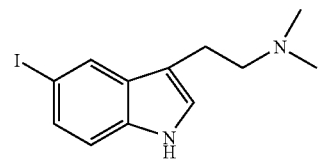

A 3 L flask is charged with 2-(5-iodo-3-hydroxy-2-oxo-2,3-dihydro-1H-indol-3-yl)-N,N-dimethyl-acetamide (Reference Example 4) (100 g, 0.277 mol), and 800 mL of DME. The suspension is cooled to −15° C., and sodium borohydride (31.5 g 96%, 0.832 mol) is added to this mixture, which causes a raise of the temperature by 5° C. To this, $BF_3$- etherate is added dropwise during 30 minutes (157.6 g, 1.11 mol). Initially there is a strong exothermic reaction (requires slow addition of BF3-etherate) and evolution of a gas. The temperature is maintained between −15 and −10° C. during the addition. The formed orange slurry is then allowed to warm slowly to ambient temperature (25-27° C.), and left stirring over night (17 h). To this mixture, then 4N NaOH (555 mL) is added and the mixture is heated under reflux for 50 minutes. Then DABCO (34.3 g) is added, and refluxing the mixture is continued for two additional hours. Then water (250 mL) is added, and the DME is removed on the rotavapor. The obtained orange slurry is then extracted with TBME (1000 mL, 2×600 mL), and the combined organic layers are washed with water (800 mL) and brine (700 mL), and concentrated on the rotavapor to about 600 mL. To the stirred residue, MnO$_2$ (72.4 g), is added, and the exothermic oxidation causes a temperature rise of 20° C. Stirring is continued for one hour, and then the MnO$_2$ is filtered off. Removal of the solvent from the filtrate gives a brown oil, which is dissolved in toluene. The toluene is extracted for three times with 4 N HCl (300 mL, 2×150 mL). After adjustment of the pH of the combined aqueous layers to about 10, the product is re-extracted with TBME (3×700 mL). The combined organic layers are washed with water (500 mL), and brine (500 mL), and after almost complete removal of the solvent on the rotavapor and standing over night at 4° C. some of the product crystallizes (39 g, 44.7%). Further concentration of the mother liquors and standing for two additional days gives another crop of the title product (9.5 g, 10.9%), while still about 20 g of material (about 22%) remains in the mother liquors.

Reference Example 6

Preparation of [2-(1-Benzyl-5-iodo-1H-indol-3-yl)-ethyl]-dimethyl-amine

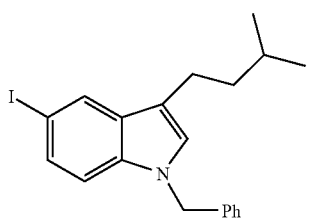

To a solution of [2-(5-iodo-1H-indol-3-yl)-ethyl]-dimethyl-amine (Reference Example 5) (35.0 g, 111.4 mmol) in DMF (250 mL), sodium hydride is added (2.81 g, 117 mmol) at RT in portions during 15 minutes. The mixture is then stirred for another 15 minutes, and then cooled to 4° C. A solution of benzyl chloride (14.1 g, 111.4 mmol) in DMF (50 mL) is added during 20 minutes, and the temperature is maintained during 4 to 8° C. The mixture is left stirring over night, and then most of the solvent is removed on the rotavapor. To the residue is added water (500 mL), and the product is extracted with TBME (2×250 mL). The organic layer is washed with brine (2×250 mL), and after removal of the solvent, 28.5 g of a brown oil is obtained. This is dissolved in ethyl acetate (500 mL) and the product is extracted with 4 N Hcl (550 mL). The product is liberated by adding 30% NaOH to the aqueous layer (300 mL), and re-extracted into ethyl acetate (500 mL). The organic layer is washed with brine (2×250 mL), and the solvent removed to leave 20.2 g of brown oil, which is crystallized from di-isopropyl ether and pentane to give the title product (17.3 g, 38%). Concentrating the aqueous layer of the first gives a precipitate (18.8 g), which is recrystallized from ethyl acetate (250 mL) to give 12.3 g of the N-benzyl ammonium chloride of the target.

Reference Example 7

Preparation of [2-(1-Benzyl-5-bromo-1H-indol-3-yl)-ethyl]-dimethyl-amine

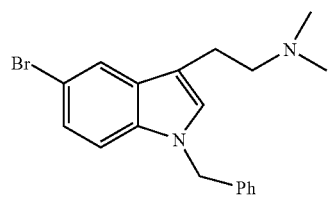

In a 100 mL flask with inner thermometer and stirrer, 3.76 g (14.1 mmol) of [2-(5-bromo-1H-indol-3-yl)-ethyl]-dimethyl-amine (Example 3) is dissolved in 40 mL of dry N,N-dimethyl formamide (DMF). To the solution NaH (95%, 366 mg, 14.5 mmol) is added under an inert atmosphere. Hydrogen gas is forming, and the NaH dissolves under slight warming during about 30 minutes. The solution is then cooled to 5° C., and a solution of benzyl chloride (1.77 g, 14 mmol) in 10 mL of DMF is added dropwise during a 10-minute period. The cooling bath is removed, and the mixture is left stirring over night at ambient temperature. Then the mixture is diluted with water (about 100 mL) and extracted with n-hexane/ether (about 1:1, 3×100 mL), and the combined organic extracts are re-extracted with water (3×100 mL). After drying and removal of the solvent, the remaining oil is chromatographed on silica (80 g, 230-400 mesh, ethyl acetate/ethanol 5:2+1% NH$_3$) to give 3.86 g (76.6%) of the title product as an oil which crystallized on standing, mp=54-55° C.

Reference Example 8

Preparation of 3-Dimethylcarbamoylmethyl-3-hydroxy-2-oxo-2,3-dihydro-1H-indole-5-carboxylic acid ethyl ester

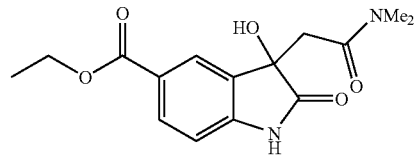

A pressure vessel is charged with 2-(5-Bromo-3-hydroxy-2-oxo-2,3-dihydro-1H-indol-3-yl)-N,N-dimethyl-acetamide (Reference Example 1) (21.92 g, 70 mmol), Pd(dppp)Cl2 (4.13 g, 7 mmol), triethyl amine (28.4 g, 0.28 mol) and ethanol (405 ml, solvent). After assembling and purging with nitrogen, the vessel is charged with carbon monoxide to a pressure of 20 bar, and the carbonylation is performed at 120° C. over night. The reaction mixture is filtered through a celite pad, and the solvent is removed on the rotavapor. The residue is kept under reflux with ethyl acetate (750 mL), and filtered. After washing the filter cake for three times with ethyl acetate (3*100 mL), the filtrate is concentrated (to ca. 300 mL), and the obtained suspension is left at 0° C. over night. The product is filtered off and dried to give 19.0 g (87%) of the title compound in the form of beige crystals.

Reference Example 9

Preparation of 3-(2-Dimethylamino-ethyl)-1H-indole-5-carbaldehyde

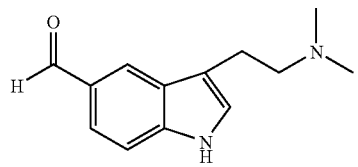

To a solution of [2-(5-bromo-1H-indol-3-yl)-ethyl]-dimethyl-amine (Reference Example 2) (15 g, 56.1 mmol) in ether (450 mL), at −75° C. a solution of tert-butyl lithium (99 ml of 1.7 N solution in hexanes, 168 mmol) is added. The mixture is stirred for 50 minutes at −75° C., and then for 30 minutes at −30° C. To the obtained beige suspension, DMF (22.5 ml) is added during 15 minutes, and then the mixture is allowed to warm to ambient temperature. The mixture is poured on water and extracted with diethyl ether (500 mL). After washing the organic layer with brine (3 times 500 mL), and drying (sodium sulfate), removal of the solvent leaves the crude aldehyde, which is recrystallized, from toluene/hexane. Yield of the title compound: 9.9 g (81.8%) yellowish plates, mp=103° C.

Where in the following Examples HPLC is mentioned, the following conditions apply: Column: Hypersil BDS-C18, 125×4 mm, eluent: Flow 1 ml/min, acetonitrile:water gradient 1% acetonitrile in water to 100% acetonitrile within 10 min, then 2 min 100% acetonitrile, 0.1% trifluoroacetic acid as additive during the whole elution, detection: UV at 254 nm;

retention times: 3-(2-dimethylamino-ethyl)-1H-indole-5-carbonitrile 4.7 min; [2-(5-Bromo-1H-indol-3-yl)-ethyl]-dimethyl-amine (Reference Example 2): 5.7 min; [2-(5-Iodo-1H-indol-3-yl)-ethyl]-dimethyl-amine (Reference Example 5): 5.7 min Example 1

Reductive Hydrazination of 3-(2-dimethylamino-ethyl)-1H-indole-5-carbonitrile to the Corresponding Hydrazone and Hydrazine

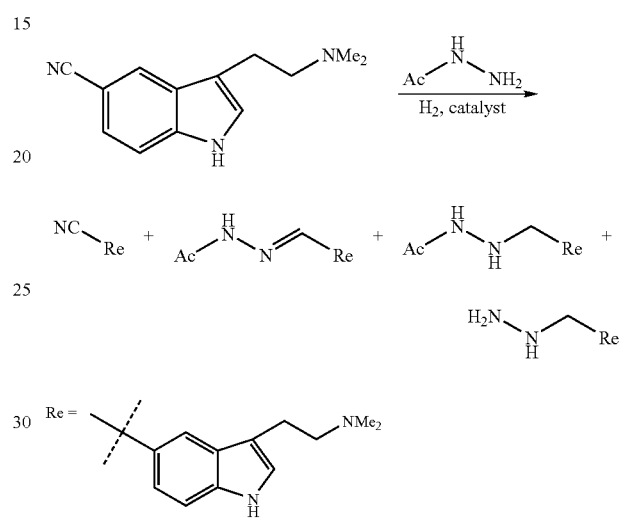

A glass vial is charged with 3-(2-dimethylamino-ethyl)-1H-indole-5-carbonitrile (Reference Example 3, Example 3 or Example 4; 100 mg, 0.47 mmol), N-acetyl hydrazine (39 mg, 0.47 mmol) and catalyst (see table). After flushing the vial with argon, methanol (3 ml) is added, and the vial transferred into an autoclave. The autoclave is purged thrice with nitrogen and then thrice with hydrogen. After a check for tightness, the hydrogenation is performed at 55 bar/105° C. over night. The hydrogen is then released, and the catalyst is removed via filtration through a millipore syringe filter. The clear filtrate is analysed by HPLC for the products the retention times are given in the table below.

The following table shows the yields when different catalysts are used:

| Catalyst | Educt | Ac-NH-N=CH-Re | Ac-NH-NH-CH₂-Re | H₂N-NH-CH₂-Re |
|---|---|---|---|---|
| Retention-time HPLC | | 4.1 min | 3.6 min | 3.3 min |
| Raney-Ni | 2% | 13% | 30% | 55% |
| Ru/C (10%) | 2% | 37% | 12% | 49% |
| Rh/C (5%) | 2% | 44% | 15% | 36% |

Example 2

Preparation of Rizatriptan

A solution of [2-(5-Hydrazinomethyl-1H-indol-3-yl)-ethyl]-dimethyl-amine (3.1 g, 85% purity, 11.9 mmol) and 1,3,5-triazine (0.69 g, 8.5 mmol) in ethanol (50 ml) is refluxed over night. The solution is then diluted with tert-butyl methylether (TBME), and the precipitated ammonium salts are filtered off. Removal of the solvent on the rotavapor produces 3.6 g of an oil which is chromatographed on silica ($CH_2Cl_2$: $MeOH:NH_4OH$ 98:2:1 to 95:5:1 v:v:v) to give 1.75 g (55%) of the product, dimethyl-[2-(5-[1,2,4]triazol-1-ylmethyl-1H-indol-3-yl)-ethyl]amine (Rizatriptan). HPLC retention time: 4.0 min.

Example 3

Synthesis of N,N-dimethyl 2-(5-cyano-1H-indol-3-yl)ethyl-amine

A flask with mechanical stirrer is charged with 5-iodo-dimethyltryptamine (179 g of 75% purity, 0.427 mol), copper (I)cyanide (90 g, 1.0 mol), and N-methylpyrrolidone (1.5 l). The pink suspension is heated at 180° C. under a nitrogen atmosphere and vigorously stirred, until the iodide is completely consumed (7 h). After cooling to ambient temperature ammonia (2 l 25% solution in water) is added, and the resulting mixture is stirred over night. The mixture is then extracted with TBME (6*1.5 l), and the combined organic layers are washed with water (3*3 l), and brine (1*3 l), and dried (sodium sulfate). Removal of the solvent leaves 75 g (82%) of the product which is >95% pure by HPLC (other properties cf. Reference Example 3).

Example 4

Synthesis of N,N-dimethyl 2-(5-cyano-1H-indol-3-yl)ethyl-amine

A flask is charged with 5-bromo-dimethyltryptamin (5.34 g, 20 mmol), copper (I)cyanide (2.69 g, 30 mmol), and N-Methylpyrrolidone (20 ml). The mixture is heated at 200° C. for 9 hours under a nitrogen atmosphere and then left stirring over night. The brown mixture is poured on water to give a brown precipitate. This is suspended in ammonia (100 ml 25% solution in water), and the mixture is stirred over night. Extraction with TBME (3*100 ml), and removal of the solvent from the dried (sodium sulfate) organic layer gives the title product as a yellow solid (properties as in Reference Example 3).

Example 5

Purification of [2-(5-Formyl-1H-indol-3-yl)-ethyl]-dimethyl ammonium chloride

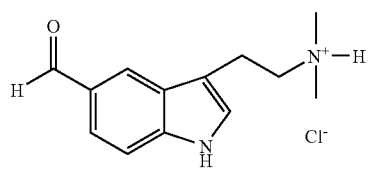

In a flask, 3-(2-dimethylamino-ethyl)-1H-indole-5-carbaldehyde (20 g, 92.5 mmol) is dissolved in ethanol (150 ml). To this solution is added a solution of HCl (11 g of 32% aqueous HCl in 100 ml of ethanol). The temperature rises to 40° C., and after the addition of activated charcoal (7.0 g) the mixture is kept at reflux for one hour and filtered. The filtrate is treated again with activated charcoal (11 g) at reflux for another 30 minutes, and from the filtrate the solvent is removed completely on the rotavapor to leave the crude salt (19.2 g). This is dissolved in refluxing ethanol (120 ml), and on 3 subsequent cooling steps with further concentration, the product is obtained as colorless nonhygroscopic needles of m.p. 220° C. $^1$H-NMR (DMSO, 300 MHz) δ 2.81 (s, 6H, $NH(CH_3)_2$); 3.21, 3.33 (2 m, 2H each, $CH_2CH_2NHMe_2$); 7.38 (d, 1H, J=2.1 Hz, H-2); 7.50 (d, 1H, J=8.5 Hz, H-7); 7.66 (dd, 1H, J=1.5 Hz, H-6); 8.25 (br s, 1H, H-4); 9.96 (s, 1H, CHO); 10.94 (br s, 1H, NH); 11.63 (s, 1H, $NHMe_2$). $^{13}$C-NMR (DMSO, 75 MHz) δ 19.39 ($CH_2$); 42.96 ($NH(CH_3)_2$); 57.63 ($CH_2NHMe_2$); 112.62 (C-3); 112.93 (C-7); 121.81 (C-6); 124.72 (C-4); 126.01 (C-2); 127.33 (C-9); 129.11 (C-5); 140.31 (C-8); 192.87 (CHO).

Example 6

Carboxy-methanecarboxylate [2-(5-formyl-1H-indol-3-yl)-ethyl]-dimethyl-ammonium

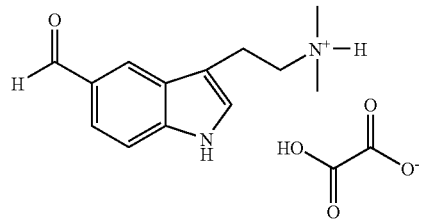

A solution of oxalic acid di-hydrate (2.91 g, 23.12 mmol) in ethanol (15 ml) is added slowly to a refluxing solution of 3-(2-Dimethylamino-ethyl)-1H-indole-5-carbaldehyde (5.0 g, 23.12 mmol) in ethanol (15 ml). On addition of ca. 70% of the oxalic acid solution, crystallization of the product as a microcrystalline solid starts. The salt is filtered off, washed twice with ethanol/ether (1:1 v:v, 15 ml each portion) and ether (30 ml) and dried to give 6.45 g (91.1%) of a cream coloured very fine leaflets. The DSC shows three endothermic regions: 150° C. (broad, probably phase transition), 168.6° C. (probably melting point) and 237.7° C. (probably decomposition). $^1$H-NMR (DMSO, 300 MHz) δ 2.84 (s, 6H, $NH(CH_3)_2$); 3.17, 3.31 (2 m, 2H each, $CH_2CH_2NHMe_2$); 7.39 (d, 1H, J=2.3 Hz, H-2); 7.52 (d, 1H, J=8.5 Hz, H-7); 7.66 (dd, 1H, J=1.9 Hz, H-6); 8.20 (v br s, 1H, NH); 8.25 (d, 1H, H-4); 9.96 (s, 1H, CHO); 11.60 (s, 1H, $NHMe_2$). $^{13}$C-NMR (DMSO, 75 MHz) δ 20.86 (CH2); 43.01 ($NH(CH_3)_2$); 57.52 ($CH_2NHMe_2$); 112.35 (C-3); 112.97 (C-7); 121.78 (C-6); 124.72 (C-4); 126.19 (C-2); 127.30 (C-9); 129.17 (C-5); 140.33 (C-8); 165.47 (oxalate); 192.91 (CHO).

Example 7

Formic acid [3-(2-dimethyl-amino-ethyl)-1H-indol-5ylmethylene] hydrazide

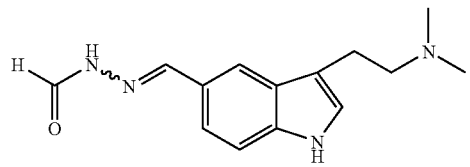

A 250 ml flask is charged with 3-(2-dimethylamino-ethyl)-1H-indole-5-carbaldehyde (material purified via the oxalate, Example 6, 4.32 g, 20 mmol), N-formylhydrazine (1.33 g 90%, 20 mmol) and ethanol (30 ml). The mixture is heated at reflux for 2½ h, then the solvent is removed on the rotavapor. The residue is dissolved in CHCl₃ (50 ml) and again evaporated (rotavapor) in order to remove the reaction water completely. The residue is dissolved in CHCl₃ (ca. 40 ml) at reflux and then allowed to cool in the heating bath over night, leading to the crystallization of the product in fine needles. Some ether (25 ml) is added in order to bring the crystallization to completion, and then the product is filtered off, washed with little ether and dried to give 4.5 g (87.2%) of the product, m.p. 163° C. (DSC). ¹H-NMR (DMSO, 300 MHz) δ 2.20 (s, 6H, N(CH₃)₂); 2.50, 2.81 (2 m, 2H each, (CH₂)₂NMe₂); 7.17 (d, 1H, J=1.8 Hz, H-2); 7.34 (d, 1H, J=8.4 Hz, H-7); 7.47 (dd, 1H, J=1.3 Hz, H-6); 7.71 (br s, 1H, H-4); 8.11 (s, 1H, N=CH); 8.67 (s, 1H, CHO); 10.97 (br, 1H, NH); 11.50 (br s, 1H, NH). ¹³C-NMR (DMSO, 75 MHz) δ 23.83 (CH₂); 45.96 (N(CH₃)₂); 60.72 (CH₂NMe₂); 112.61 (C-7); 114.46 (C-3); 119.54, 119.70 (C-4 and C-6); 124.29 (C-2); 125.15 (C-5); 127.93 (C-9); 138.06 (C-8); 147.74 (CH=N); 156.11 (CHO).

Example 8

{2-[5-(Methoxycarbonyl-hydrazonomethyl)-1H-indol-3-yl]-ethyl}-dimethyl-ammonium; chloride

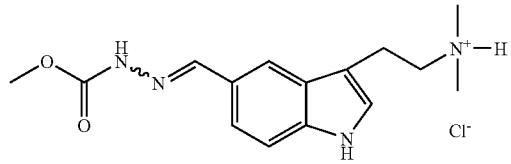

A 50 ml flask is charged with [2-(5-Formyl-1H-indol-3-yl)-ethyl]-dimethyl-ammonium chloride (1.55 g, 6.13 mmol) and hydrazinecarboxylic acid methyl ester (0.55 g, 6.13 mmol). Both compounds are dissolved in warm ethanol (10 ml), and then the solvent is removed on the rotavapor (60° C./240 mbar). The residue is re-dissolved in ethanol (20 ml), and solvent and reaction water are again removed on the rotavapor. The remaining foam is dissolved in isopropanol (15 ml), and after prolonged stirring at 70° C. the material crystallizes. The product is filtered off and dried to give 1.89 g (94.9%) of pale yellow crystals, mp=226° C. (DSC). ¹H-NMR (DMSO, 300 MHz) δ 2.80 (s, 6H, N(CH₃)₂); 3.16, 3.30 (2 m, 2H each, (CH₂)₂NMe₂); 3.67 (s, 3H, OCH₃); 7.25 (d, 1H, J=2.3 Hz, H-2); 7.38 (d, 1H, J=8.24 Hz, H-7); 7.49 (dd, 1H, J=1.4 Hz, H-6); 7.77 (br s, 1H, H-4); 8.15 (s, 1H, N=CH); 10.92, 11.00 (2 br s, 1H each, NH, NH+); 11.30 (s, 1H, H-1). ¹³C-NMR (DMSO, 75 MHz) δ 20.79 (CH₂); 41.19 (N(CH₃)₂); 52.53 (OCH₃); 57.32 (CH₂NMe₂); 110.77 (C-7); 112.83 (C-3); 119.48, 119.88 (C-4 and C-6); 124.83 (C-2); 126.04 (C-5); 127.32 (C-9); 137.66 (C-8); 146.54 (CH=N); 154.72 (NCO).

Example 9

N'-[3-(2-Dimethylamino-ethyl)-1H-indol-5-ylmethylene]hydrazine-carboxylic acid methyl ester

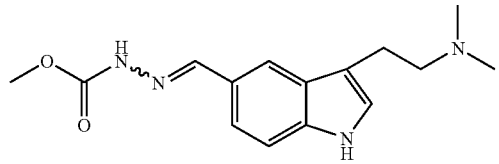

To a solution of hydrazinecarboxylic acid methyl ester (0.90 g, 10 mmol) in methanol (10 ml) is added 3-(2-Dimethylamino-ethyl)-1H-indole-5-carbaldehyde (2.16 g, 10 mmol), and the mixture obtained is heated at reflux for 20 hours. After removal of the solvent, a yellow oil (3.0 g) is obtained, which is chromatographed on silica (chloroform:methanol 9:1 v:v to 4:1 v:v) to give 1.6 g (55.4%) of the product as a colourless foam. ¹H-NMR (CDCl₃, 300 MHz) δ 2.26 (s, 6H, N(CH₃)₂); 2.57, 2.84 (2 m, 2H each, CH₂CH₂NHMe₂); 3.79 (s, 3H, OCH₃); 6.90 (s, 1H, H-2); 7.11 (d, 1H, J=8.5 Hz, H-7); 7.45 (dd, 1H, J=1.5 Hz, H-6); 7.62 (br s, 1H, H-4); 7.77 (s, 1H, N=CH); 9.04 (br s, 1H, H-1); 9.33 (br s, 1H, NH). ¹³C-NMR (CDCl₃, 75 MHz) δ 23.73 (CH₂); 45.51 (N(CH₃)₂); 53.04 (OCH₃); 60.39 (CH₂NMe₂); 112.07 (C-7); 114.66 (C-3); 119.52 (C-4); 120.72 (C-6); 123.14 (C-2); 125.14 (C-5); 127.52 (C-9); 137.71 (C-8); 147.25 (N=CH); 155.02 (NC=O).

Example 10

N'-[3-(2-Dimethylamino-ethyl)-1H-indol-5-ylmethylene]-hydrazine-carboxylic acid isobutyl ester

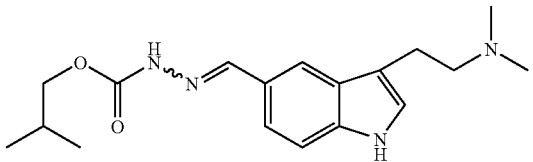

A 100 ml flask is charged with 3-(2-dimethylamino-ethyl)-1H-indole-5-carbaldehyde (Reference Example 9; 2.16 g, 10 mmol), methanol (50 ml), and hydrazinecarboxylic acid isobutyl ester (1.32 g, 10 mmol). This mixture is heated at reflux, and after 6 hours the conversion is 70% by NMR. Heating is continued over night, and removal of the solvent gives the crude product, which is then filtered over a pad of silica (40 g) with the following eluent: CH₂Cl₂:methanol:NEt₃ 90:10:1 (v:v:v), ca. 700 ml. Removal of the solvent gives the product (2.82 g, 85%) as a pale yellow residue which is pure by NMR. ¹H-NMR (CDCl₃, 300 MHz) δ 0.93 (d, 6H, J=6.5 Hz, CH(CH₃)₂); 1.96 (m, 1H, CH(CH₃)₂); 2.22 (s, 6H, N(CH₃)₂); 2.52, 2.78 (2 m, 2H each, CH₂CH₂NHMe₂); 3.97 (d, 2H, J=6.5 Hz, OCH₂); 6.85 (s, 1H, H-2); 7.04 (d, 1H, J=7.6 Hz, H-7); 7.41 (dd, 1H, J=1.5 Hz, H-6); 7.61 (bs, 1H, H-4); 7.86 (br s, 1H, N=CH); 9.43 (br s, 1H, NH); 9.82 (br s, 1H, H-1). ¹³C-NMR (CDCl3, 75 MHz) δ 19.36 (CH(CH₃)₂); 23.59 (CH₂); 28.39 (CH(CH₃)₂); 45.53 (N(CH₃)₂); 60.32 (CH₂NMe₂); 71.87 (OCH₂); 112.20 (C-7); 114.21 (C-3); 119.35 (C-4); 120.58 (C-6); 123.41 (C-2); 125.17 (C-5); 127.48 (C-9); 137.76 (C-8); 146.80 (N=CH); 154.91 (NC=O).

Example 11

N'-[3-(2-Dimethylamino-ethyl)-1H-indol-5-ylmethylene]-hydrazinecarboxylic acid tert-butyl ester

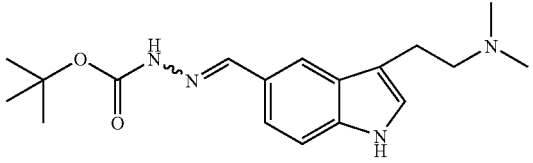

A 100 ml flask is charged with 3-(2-dimethylamino-ethyl)-1H-indole-5-carbaldehyde (Reference Example 9; 2.16 g, 10 mmol), hydrazinecarboxylic acid tert-butyl ester (1.32 g, 10 mmol), and methanol (10 ml). This mixture is heated at reflux for 18 hours, and then the solvent is removed on the rotavapor to leave the hydrazone (3.24 g, 98%). ¹H-NMR (CDCl₃, 300 MHz) δ 1.55 (s, 9H, C(CH₃)₃); 2.30 (s, 6H, N(CH₃)₂); 2.59, 2.87 (2 m, 2H each, CH₂CH₂NHMe₂); 6.94 (d, 1H, J=2 Hz, H-2); 7.17 (d, 1H, J=8.5 Hz, H-7); 7.52 (dd, 1H, J=1.5 Hz, H-6); 7.68 (d, 1H, H-4); 7.84 (br s, 1H, N=CH); 8.42 (br s, NH); 9.10 (s, 1H, H-1). ¹³C-NMR (CDCl₃, 75 MHz) δ 23.89 (CH₂); 28.83 (C(CH₃)₃); 45.66 (N(CH₃)₂); 60.47 (CH₂NMe₂); 81.23 (OCMe₃); 111.94 (C-7); 114.77 (C-3); 119.30 (C-4); 120.76 (C-6); 122.91 (C-2); 125.37 (C-5); 127.48 (C-9); 137.54 (C-8); 146.13 (N=CH); 153.13 (NC=O).

Example 12

N'-[3-(2-Dimethylamino-ethyl)-1H-indol-5-ylmethylene]-hydrazinecarboxylic acid benzyl ester

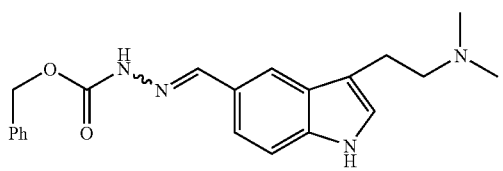

A 50 ml flask is charged with 3-(2-dimethylamino-ethyl)-1H-indole-5-carbaldehyde (Reference Example 9; 2.16 g, 10 mmol), hydrazinecarboxylic acid benzyl ester (1.66 g, 10 mmol), and methanol (30 ml). This mixture is heated at reflux over night, and then the solvent is removed on the rotavapor to leave the hydrazone as a foam. ¹H-NMR (CDCl₃, 300 MHz) δ 2.24 (s, 6H, N(CH₃)₂); 2.55, 2.81 (2 m, 2H each, CH₂CH₂NHMe₂); 5.22 (s, 2H, OCH₂); 6.86 (d, 1H, J=2 Hz, H-2); 7.09 (d, 1H, J=8.5 Hz, H-7); 7.23-7.36 (m, Ph-H); 7.43 (dd, 1H, J=1.5 Hz, H-6); 7.62 (d, 1H, H-4); 7.79 (br s, 1H, N=CH); 9.35 (br s, NH); 9.50 (s, 1H, H-1). ¹³C-NMR (CDCl₃, 75 MHz) δ 23.57 (CH₂); 45.36 (N(CH₃)₂); 60.26 (CH₂NMe₂); 67.47 (OCH₂); 112.17 (C-7); 114.3 (C-3); 119.51 (C-4); 120.69 (C-6); 123.32 (C-2); 125.15 (C-5); 127.48 (C-9); 128.33, 128.50 (2C), 128.73 (2C), 136.40 (q) (Ph C); 137.76 (C-8) 147.50 (N=CH); 154.10 (NC=O).

Example 13

Formic acid N'-[3-(2-dimethylamino-ethyl)-1H-indol-5-ylmethyl]-hydrazide

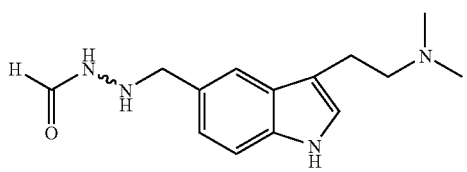

A 50 ml pressure reactor is charged with formic acid [3-(2-dimethyl-amino-ethyl)-1H-indol-5ylmethylene] hydrazide (Example 7; 3.0 g, 11.6 mmol), methanol (30 ml), and palladium on charcoal (0.6 g of 5% Pd-content type E-4522). After sealing, the pressure vessel is purged with argon (three times), heated in an oil bath to 45° C., and then pressurized with hydrogen (23.1 bar). After stirring over night, more catalyst (0.6 g of 5% Pd-content type E-4522) is added, and the hydrogenation allowed to proceed for another 18 hours. The reaction mixture is then filtered over a pad of Hyflo, and the solvent removed from the filtrate on the rotavapor to give the product (2.6 g, 86%) as a pale yellow residue.

The product is also prepared as follows: A 300 ml pressure reactor equipped with a hollow-shaft propeller stirrer is charged with formic acid [3-(2-dimethyl-amino-ethyl)-1H-indol-5ylmethylene] hydrazide (12.3 g, 47.6 mmol), methanol (125 ml), and palladium on charcoal (2.5 g of 5% Pd-content type E-4522). After sealing, the pressure vessel is purged with argon (three times), pressurized with hydrogen (38.0 bar) and then heated to 45° C. After stirring for 48 h, the vessel is allowed to cool down and is vented. The reaction mixture is filtered over a pad of Hyflo, and the solvent removed from the filtrate on the rotavapor to give the product (11.9 g, 95%) as a pale yellow foam.

¹H-NMR (DMSO-D6, 300 MHz) δ 2.27 (s, 6H, N(CH₃)₂); 2.58, 2.82 (2 m, 2H each, CH₂CH₂NHMe₂); 3.93 (s, 2H, CH₂NH); 5.37 (br s, 1H, NH); 7.04 (dd, 1H, J=8.2 Hz, J=1.5 Hz, H-6); 7.11 (d, 1H, J=2 Hz, H-2); 7.26 (d, 1H, H-7); 7.43 (brs, 1H, H-4); 7.86 (d, J=10.5 Hz), 7.90 (s) (together 1H, NHCHO); 8.76 (d, J=10.5 Hz), 9.32 (s) (together 1H, NHCHO); 10.75 (s, 1H, H-1).

Example 14

N'-[3-(2-Dimethylamino-ethyl)-1H-indol-5-ylmethyl]-hydrazinecarboxylic acid methyl ester

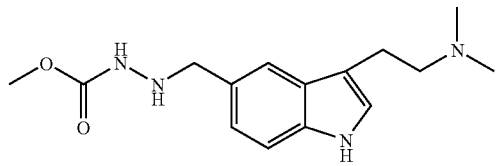

A 50 ml pressure vessel is charged with N'-[3-(2-dimethylamino-ethyl)-1H-indol-5-ylmethylene]hydrazine-carboxylic acid methyl ester (Example 9; 793 mg, 2.74 mmol), ethanol (10.8 ml), and the catalyst (5% Pd/C type E-4522, 158.6 mg). The vessel is sealed and purged with argon (three times), heated in an oil bath to 50° C., and then pressurized with hydrogen (75.4 bar). The stirrer is started (800 rpm), and the hydrogenation allowed to proceed over night. After cooling to ambient temperature the pressure vessel is vented, and the reaction mixture filtered over a pad of Hyflo to remove the catalyst. Removal of the solvent gives the product as a pale yellow residue (707 mg, 88.9%), which is pure by NMR.

¹H-NMR (CD₃OD, 300 MHz) δ 2.81 (s, 6H, N(CH₃)₂); 3.10, 3.30 (2 m, 2H each, CH₂CH₂NHMe₂); 3.53 (s, 3H, OCH₃); 3.91 (s, 2H, CH₂N); 7.04 (dd, 1H, J=8.3 Hz, J=1.5 Hz, H-6); 7.11 (s, 1H, H-2); 7.24 (d, 1H, H-7); 7.53 (s, 1H, H-4). ¹³C-NMR (CD₃OD, 75 MHz) δ 22.33 (CH₂); 43.91 (N(CH₃)₂); 53.08 (OCH₃); 57.76 (CH₂N); 59.45 (CH₂NMe₂); 110.05 (C); 112.93 (CH); 120.08 (CH); 124.77 (CH); 125.34 (CH); 128.54 (C); 129.41 (C); 138.24 (C); 160.32 (C=O).

Example 15

N'-[3-(2-Dimethylamino-ethyl)-1H-indol-5-ylmethyl]-hydrazinecarboxylic acid isobutyl ester

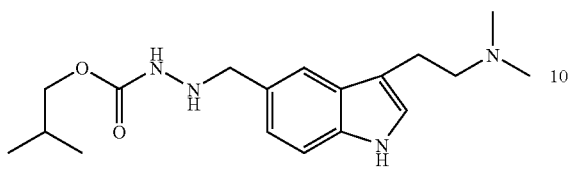

A 50 ml pressure vessel is charged with N'-[3-(2-Dimethylamino-ethyl)-1H-indol-5-ylmethylene]-hydrazinecarboxylic acid isobutyl ester (Example 10; 1.76 g, 5.33 mmol), ethanol (25 ml), and the catalyst (5% Pd/C type E-4522, 325 mg). The vessel is sealed, purged with argon (three times and hydrogen (three times), heated in an oil bath to 65° C., and then pressurized with hydrogen (78.4 bar). The stirrer is started (900 rpm), and the hydrogenation allowed to proceed for 21.5 hours. After cooling to ambient temperature the pressure vessel is vented, and the reaction mixture filtered over a pad of Hyflo to remove the catalyst. Removal of the solvent gives the product as a pale yellow residue, which is pure by NMR. $^1$H-NMR (CD$_3$OD, 300 MHz) δ 0.81 (d, 6H, J=6.8 Hz, CH(CH$_3$)$_2$); 1.78 (m, 1H, CH(CH$_3$)$_2$); 2.27 (s, 6H, N(CH$_3$)$_2$); 2.61, 2.83 (2 m, 2H each, CH$_2$CH$_2$NHMe$_2$); 3.74 (d, 2H, J=6.6 Hz, OCH$_2$); 3.90 (s, 2H, CH$_2$N); 6.95 (s, 1H, H-2); 7.02 (dd, 1H, J=8.3 Hz, J=1.5 Hz, H-6); 7.19 (d, 1H, H-7); 7.43 (s, 1H, H-4). $^{13}$C-NMR (CD$_3$OD, 75 MHz) δ 19.70 (CH$_3$); 24.46 (CH$_2$); 29.71 (CHMe$_2$); 45.65 (N(CH$_3$)$_2$); 57.89 (CH$_2$N); 61.64 (CH$_2$NMe$_2$); 72.57 (OCH$_2$); 112.64 (CH); 113.85 (C); 120.42 (CH); 124.06 (CH); 124.33 (CH); 128.89 (C); 129.09 (C); 138.13 (C); 160.03 (C=O).

Example 16

N'-[3-(2-Dimethylamino-ethyl)-1H-indol-5-ylmethyl]-hydrazinecarboxylic acid tert-butyl ester

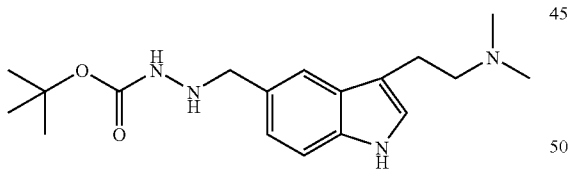

A 50 ml pressure vessel is charged with N'-[3-(2-Dimethylamino-ethyl)-1H-indol-5-ylmethylene]-hydrazinecarboxylic acid tert-butyl ester (Example 11; 1.20 g, 3.63 mmol), ethanol (18 ml), and the catalyst (5% Pd/C type E-4522, 240 mg). The vessel is sealed, purged with argon (three times and hydrogen (three times), heated in an oil bath to 87° C., and then pressurized with hydrogen (43.4 bar). The stirrer is started (900 rpm), and the hydrogenation allowed to proceed for 18 hours. After cooling to ambient temperature the pressure vessel is vented, and the reaction mixture filtered over a pad of Hyflo to remove the catalyst. Removal of the solvent gives the product (1.092 g, 90.4%) as a pale yellow residue, which is pure by NMR. $^1$H-NMR (CD$_3$OD, 300 MHz) δ 1.33 (s, 9H, C(CH$_3$)$_3$); 2.45 (s, 6H, N(CH$_3$)$_2$); 2.84-2.96 (m, 4H, CH$_2$CH$_2$NMe$_2$); 3.88 (s, 2H, CH$_2$N); 7.00 (br s, 1H, H-2); 7.02 (dd, 1H, J=8.3 Hz, J=1.5 Hz, H-6); 7.21 (d, 1H, H-7); 7.45 (s, 1H, H-4). $^{13}$C-NMR (CD$_3$OD, 75 MHz) δ 23.69 (CH$_2$); 29.11 (C(CH$_3$)$_3$); 45.03 (N(CH$_3$)$_2$); 57.94 (CH$_2$N); 60.66 (CH$_2$NMe$_2$); 112.41 (C); 112.74 (CH); 120.30 (CH); 124.53 (CH); 128.89 (C); 129.15 (C); 138.17 (C); 162.32 (br, C=O).

Example 17

{2-[5-(N'-Methoxy carbonyl-hydrazinomethyl)-1H-indol-3-yl]-ethyl}-dimethyl-ammonium; chloride

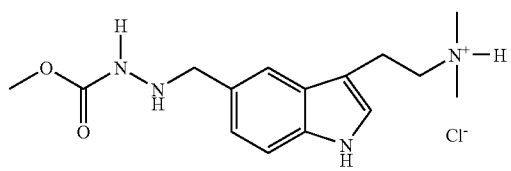

A vial in a 50 ml pressure vessel is charged with {2-[5-(methoxycarbonyl-hydrazonomethyl)-1H-indol-3-yl]-ethyl}-dimethyl-ammonium chloride (Example 8; 100 mg, 0.308 mmol), methanol (1.5 ml), and the catalyst (5% Pd/C type E-4522, 20 mg). The vessel is sealed and purged with argon (three times) and hydrogen (three times), and then pressurized with hydrogen (10 bar). The stirrer is started (800 rpm), and the hydrogenation allowed to proceed for 3¾ hours. Then the pressure vessel is vented, and the reaction mixture filtered over a syringe filter. Removal of the solvent gives the product as pale yellow residue, which is pure by NMR.

Example 18

Formic acid N'-[3-(2-dimethylamino-ethyl)-1H-indol-5-ylmethyl]-hydrazide, dihydrochloride

A solution of HCl in ether (49.1 ml of a 2.138 molar solution, 105 mmol) is added under a nitrogen atmosphere to a solution of formic acid N'-[3-(2-dimethylamino-ethyl)-1H-indol-5-ylmethyl]-hydrazide (Example 13; 26.03 g, 100 mmol) in THF (300 ml) within 10 minutes. The obtained thick suspension of the product is filtered, and the filter cake washed with THF (ca. 80 ml) and ether (ca. 100 ml). The product is dried over night to give 28.04 g (84%) of cream colored hygroscopic crystals. $^1$H-NMR (DMSO-D6, 300 Mhz) □ 2.81 (s, 6H, HN$^+$(CH$_3$)$_2$); 3.13 (m, 2H, CH$_2$); 3.30 (m, 2H, CH$_2$); 4.05 (s, 2H, CH$_2$N$^+$); 7.10 (dd, 1H, J=8.3 Hz, J=1.7 Hz, H-6); 7.21 (d, J=2.6 Hz, H-2); 7.32 (d, 1H, H-7); 7.63 (d, 1H, H-4); 7.96 (s, 1H, CHO); 10.9-11.15 (brs, H+); 11.10 (d, 1H, NH).

Example 19

Dimethyl-[2-(5-[1,2,4]triazol-1-ylmethyl-1H-indol-3-yl)-ethyl]-amine (Rizatriptane)

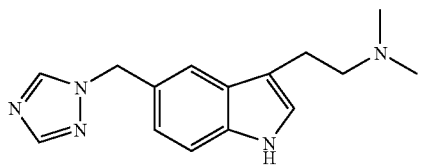

A solution of the dihydrochloride of formic acid N'-[3-(2-dimethylamino-ethyl)-1H-indol-5-ylmethyl]-hydrazide (Example 18; 6.665 g, 20 mmol), and 1,3,5-triazine (1.081 g, 13.3 mmol) in ethanol (50 ml) is heated at reflux for six hours under a nitrogen atmosphere. From the slightly hazy yellow solution, the solvent is removed on the rotavapor, and the yellow residue is stirred with sodium hydroxide (100 ml 2N solution) and chloroform (100 ml). The organic layer is separated, washed with water (100 ml) and brine (100 ml) and dried (sodium sulfate). Removal of the solvent gives the product (4.54 g, 84%) as a slightly brown oil which solidifies on standing. $^1$H-NMR (CDCl$_3$, 300 MHz) δ 2.26 (s, 6H, N(CH$_3$)$_2$); 2.56 (m, 2H, CH$_2$); 2.83 (m, 2H, CH$_2$NMe$_2$); 5.27 (s, 2H, CH$_2$N); 6.88 (d, 1H, J=2.0 Hz, H-2); 6.92 (dd, 1H, J=8.2 Hz, J=1.8 Hz, H-6); 7.15 (d, 1H, H-7); 7.40 (d, 1H, H-4); 7.84 (s, 1 H, triazol H-?); 7.89 (s, 1H, triazol H-?); 9.24 (br s, 1H, NH). $^{13}$C-NMR (CDCl$_3$, 75 MHz) δ 23.68 (CH$_2$); 45.50 (N(CH$_3$)$_2$); 54.88 (CH$_2$N); 60.31 (CH$_2$NMe$_2$); 112.18 (C-7); 114.01 (C-3); 119.26 (C-4); 122.26 (C-6); 123.24 (C-2); 124.94 (C-5); 127.87 (C-9); 136.53 (C-8); 143.00 (triazol C-5); 151.88 (triazol C-3).

Example 20

Dimethyl-[2-(5-[1,2,4]triazol-1-ylmethyl-1H-indol-3-yl)-ethyl]-ammonium benzoate (Rizatriptan benzoate)

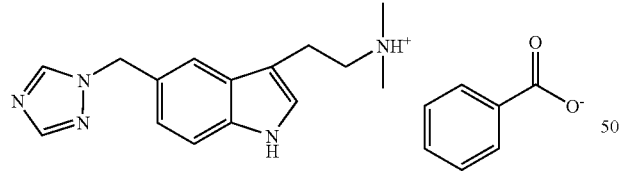

A solution of dimethyl-[2-(5-[1,2,4]triazol-1-yl-methyl-1H-indol-3-yl)-ethyl]amine (Rizatriptan, Example 19, 4.58 g, 17 mmol) in iso-propanol (40 ml) is heated to 42° C. under an atmosphere of nitrogen. To this solution is added a solution of benzoic acid (2.08 g, 17 mmol) in warm (42° C.) isopropanol (20 ml) slowly within 15 minutes. The mixture thus obtained is kept at 42° C. and stirred for another hour. After seeding with ca. 5 mg of Rizatriptan benzoate, the solution is left standing over night at −20° C. Then the flask is allowed to warm to ambient temperature and stirred for another hour. The crystals are filtered off, washed twice with little iso-propanol and ether and dried to give 3.53 g of product. Solvent removal from the mother liquors on the rotavapor, was recrystallization of the residue from isopropanol (12 ml) gives another crop of product (0.72 g). Total yield 4.25 g (63.8%), mp 180° C. (DSC). $^1$H-NMR (CDCl$_3$, 300 MHz) δ 2.57 (s, 6H, N(CH$_3$)$_2$); 2.91 (m, 2H, CH$_2$NMe$_2$); 3.00 (m, 2H, CH$_2$); 5.23 (s, 2H, CH$_2$N); 6.81 (s, 1H, H-2); 6.93 (dd, J=8.2 Hz, J=1.6 Hz, H-6); 7.17 (d, 1H, H-7); 7.28 (m, 2H, Bz meta H); 7.33 (m, 1H, Bz para H); 7.46 (d, 1H, H-4); 7.84 (s, 1H, triazol H-3); 7.87 (s, 1H, triazol H-5); 8.01 (m, 2H, Bz ortho H); 9.25 (br s, 1H, NH). $^{13}$C-NMR (CDCl$_3$, 75 MHz) δ 21.70 (CH$_2$); 43.51 (N(CH$_3$)$_2$); 54.75 (CH$_2$N); 58.48 (CH$_2$NMe$_2$); 111.86 (C-3); 112.34 (C-7); 119.13 (C-4); 122.56 (C-6); 123.51 (C-2); 125.43 (C-5); 127.48 (C-9); 128.19 (Bz meta C); 129.71 (Bz ortho C); 131.38 (Bz para C); 135.23 (Bz ipso C); 136.50 (C-8); 143.02 (triazol C-5); 151.87 (triazol C-3); 172.42 (BzCOO$^-$).

The invention claimed is:

1. A process for the manufacture of a 1,2,4-triazol-1-yl compound of the formula [A] or a salt thereof,

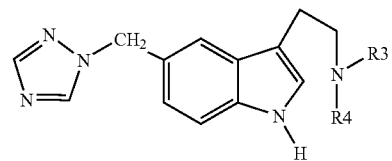

[A]

wherein each of R3 and R4 is independently hydrogen or a lower alkyl with up to and including maximally 7 carbon atoms, said process comprising the steps of:
reacting with a 1,2,4-triazolyl forming reagent a hydrazine compound of the formula [B] or a salt thereof,

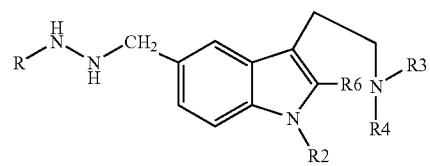

[B]

wherein R is hydrogen or acyl, R2 is hydrogen, each of R3 and R4 is independently hydrogen or a lower alkyl with up to and including maximally 7 carbon atoms, and R6 is hydrogen, further wherein, if R is acyl in formula [B], optionally removing an acyl group R before reacting the compound of the formula [B] with the 1,2,4-triazolyl forming reagent, removing any protecting group R2 and removing any group COOR7 to produce the compound of the formula [A], or a salt thereof.

2. The process according to claim 1, wherein the 1,2,4-triazol-1-yl compound of the formula [A] is Rizatriptan (3-[2-(dimethylamino)ethyl]-5-(1,2,4-triazol-1-ylmethyl)indole).

3. The process according to claim 1, further comprising an additional step selected the group consisting of (a) converting a salt of a resulting compound of the formula [A] into a free form of a compound of the formula [A], (b) converting a resulting free form of a compound of the formula [A] into a salt, and (c) converting a salt of a compound of the formula [A] into a different salt of a compound of the formula [A].

4. The process according to claim 1, where R in the compound of formula [B] is selected from the group consisting of hydrogen, formyl and C$_2$-C$_7$alkanoyl, and wherein if C$_2$-C$_7$alkanoyl is present, it is hydrolytically removed prior to the reaction with the 1,2,4-triazolyl forming reagent, and wherein each of formulae [A] and [B], each of R3 and R4 is methyl and the compound of the formula [A] is produced in free form or in the form of a pharmaceutically acceptable salt.

5. The process according to claim 1, where the 1,2,4-triazolyl forming reagent is selected from the group consisting of 1,3,5-triazine, formamidine, formamidinium salts, and formamide.

6. The process according to claim 1, wherein, prior to the reaction with the 1,2,4-triazolyl forming reagent, the compound of the formula [B] as defined in claim 1 is reacted with 1 or 2 equivalents of a protic acid to convert it into its mono- or diammonium salt, and then purified by crystallization or recrystallization.

7. A compound of the formula [B] or a salt thereof comprising

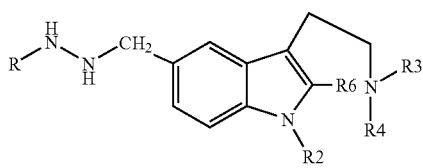

[B]

wherein:
R is hydrogen or acyl, R2 is hydrogen, each of R3 and R4 is independently hydrogen or a lower alkyl with up to an including maximally 7 carbon atoms, and R6 is hydrogen.

8. The process of claim 1, wherein the compound of formula [B] or a salt thereof is obtained by reducing a compound of the formula [D] or a salt thereof,

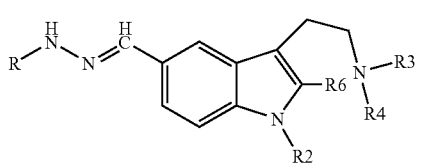

[D]

wherein R, R2, R3, R4 and R6 are defined as in claim 1.

9. The process of claim 8, wherein R is hydrogen or an alkanoyl with up to and including maximally 7 carbon atoms, further wherein each of R3 and R4 is methyl.

10. The process of claim 8, wherein the compound of formula [D] or salt thereof is obtained by reacting under reductive conditions a compound of the formula [E] or a salt thereof,

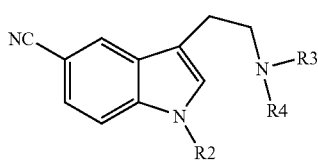

[E]

with a hydrazine compound of the formula [F] or a salt thereof,

[F]

wherein R, R2, R3 and R4 are defined as in claim 8.

11. The process of claim 10, wherein R is hydrogen or an alkanoyl with up to and including maximally 7 carbon atoms, and each of R3 and R4 is methyl.

12. The process of claim 10, wherein the compound of the formula [E] is obtained by reacting with a cyanide salt, optionally in the presence of a catalyst, a compound of the formula [G] or a salt thereof,

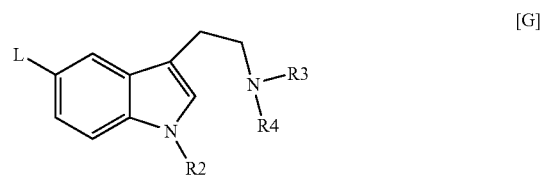

[G]

wherein R2, R3 and R4 are as defined in claim 10, and L is selected from the group consisting of halogen, unsubstituted and substituted alkanesulfonyloxy and unsubstituted or substituted arylsulfonyloxy.

13. The process of claim 12, wherein the compound of the formula [G] or salt thereof is obtained by:
(a) reducing in the presence of borane a compound of the formula [H] or a salt thereof,

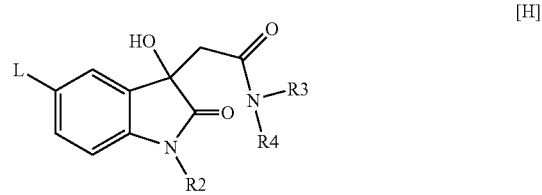

[H]

wherein R2, R3, R4 and L are as defined in claim 12, and
(b) subjecting the resulting product(s) to removal of borane from any amino borane intermediates and to a subsequent oxidation/de-hydrogenation with an oxidant to thereby yield the compound of the formula [G] or salt thereof.

14. The process of claim 1, wherein the compound of formula [B] or salt thereof is obtained by:
(a) reducing in the presence of borane a compound of the formula [C] or a salt thereof,

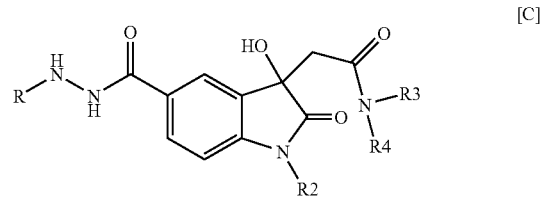

[C]

wherein R, R2, R3 and R4 are defined as in claim 1, and
(b) subjecting the resulting product(s) to removal of borane from any amino borane intermediates and to a subsequent oxidation/de-hydrogenation with an oxidant to yield the compound of the formula [B] or salt thereof.

15. The process of claim 14, wherein the compound of formula [C] or salt thereof is obtained by reacting a compound of the formula [N] or a salt thereof,

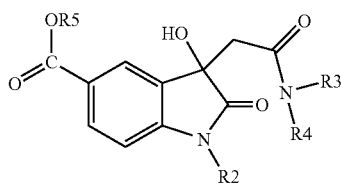

[N]

with a hydrazine of the formula [F] or a salt thereof,

[F]

wherein R, R2, R3 and R4 are defined as in claim 14, and R5 is unsubstituted or substituted alkyl.

16. The process of claim 15, wherein R5 in formula [N] is an alkyl with up to and including maximally 7 carbon atoms, and/or R in formula [F] is hydrogen.

17. The process of claim 15, wherein the compound of the formula [N] is obtained by reacting a compound of the formula [H] or a salt thereof

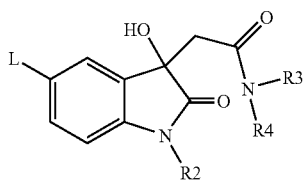

[H]

with carbon monoxide in the presence of a corresponding alcohol R5-OH, a catalyst and a tertiary nitrogen base, wherein R2, R3, R4 and R5 are as defined in claim 15 and L is selected from the group consisting of halogen, unsubstituted and substituted alkanesulfonyloxy and unsubstituted or substituted arylsulfonyloxy.

18. The process of claim 8, wherein the compound of formula [B] or salt thereof is obtained by reacting an aldehyde of the formula [O] or a salt thereof,

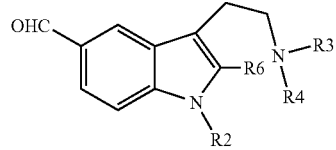

[O]

with a hydrazine compound of the formula [F] or a salt thereof,

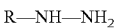

[F]

wherein R, R2, R3, R4 and R6 are defined as in claim 8.

19. The process according to claim 18, wherein R is selected from the group consisting of hydrogen, formyl and $C_2$-$C_7$alkanoyl, R2 is a protecting group or hydrogen, and each of R3 and R4 are methyl.

20. The process according to claim 19, where the compound of the formula [O] or salt thereof is obtained by reacting a compound of the formula [G] or a salt thereof,

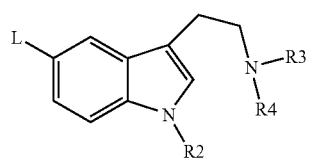

[G]

first with a lithium alkyl compound to form a lithio derivative and then with DMF or triethyl formate to obtain a corresponding compound of the formula [O] or a salt thereof after hydrolysis, wherein each of R2, R3 and R4 is as defined in claim 9 and L is halogen.

* * * * *